(12) United States Patent
Sierra

(10) Patent No.: US 6,518,290 B1
(45) Date of Patent: Feb. 11, 2003

(54) SUBSTITUTED OXAZOLES AND THIAZOLES DERIVATIVES AS HPPAR ALPHA ACTIVATORS

(76) Inventor: Michael Lawrence Sierra, GlaxoSmithKline, Five Moore Dr., P.O. Box 13398, Research Triangle Park, NC (US) 27709

( * ) Notice: Subject to any disclaimer, the term of this patent is extended or adjusted under 35 U.S.C. 154(b) by 0 days.

(21) Appl. No.: 10/148,765

(22) PCT Filed: Nov. 30, 2000

(86) PCT No.: PCT/EP00/11995

§ 371 (c)(1),
(2), (4) Date: May 31, 2002

(87) PCT Pub. No.: WO01/40207

PCT Pub. Date: Jun. 7, 2001

(30) Foreign Application Priority Data

Dec. 2, 1999 (GB) ............................................... 9928561
Feb. 15, 2000 (GB) ............................................... 0003500

(51) Int. Cl.[7] .................... A61K 31/421; A61K 31/426; C07D 277/56; C07D 263/34
(52) U.S. Cl. ...................... 514/365; 514/342; 514/374; 546/270.4; 546/271.4; 548/200; 548/236
(58) Field of Search ................................ 548/200, 236; 514/365, 342, 374; 546/270.4, 271.4

(56) References Cited

FOREIGN PATENT DOCUMENTS

| WO | WO 97 36579 | 10/1997 |
|---|---|---|
| WO | WO 99 18066 | 4/1999 |
| WO | WO 99 46232 | 9/1999 |

*Primary Examiner*—Laura L. Stockton
(74) *Attorney, Agent, or Firm*—Robert H. Brink

(57) ABSTRACT

A compound of formula (I) and pharmaceutically acceptable salts, solvates and hydrolysable esters thereof (I)

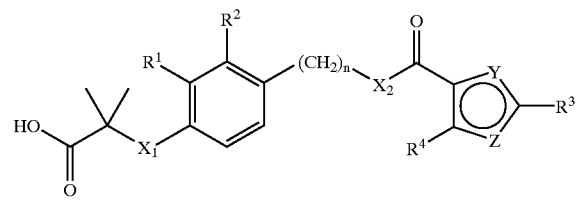

wherein;

$X_1$ represents O or S;

$R^1$ and $R^2$ independently represent H, halogen, $-CH_3$ and $-OCH_3$;

n represents 1 or 2;

$X_2$ represents NH, $NCH_3$ or O;

One of Y and Z is N, and the other is O or S;

$R^3$ represents phenyl or pyridyl (wherein the N is in position 2 or 3) and is optionally substituted by one or more halogen, $NO_2$, $NH_2$, $CF_3$, $OCF_3$, $OC_{1-6}$ straight or branched alkyl, $C_{1-6}$ straight or branched alkyl, alkenyl or alkynyl with the provision that when $R^3$ is pyridyl, the N is unsubstituted;

$R^4$ represents $CF_3$ or $CH_3$

22 Claims, No Drawings

SUBSTITUTED OXAZOLES AND THIAZOLES DERIVATIVES AS HPPAR ALPHA ACTIVATORS

CROSS-REFERENCES TO RELATED APPLICATIONS

This application is rule 371 Application of PCT Application No. PCT/EP00/11995, filed Nov. 30, 2000, which claims priority to GB Application Serial No. 9928561.1, filed Dec. 2, 1999 and GB Application Serial No. 0003500.6, filed Feb. 15, 2000.

BACKGROUND OF THE INVENTION

The present invention relates to certain novel compounds. In particular, the present invention relates to compounds that activate the alpha subtype of the human peroxisome proliferator activated receptor ("hPPAR alpha"). The present invention also relates to methods for preparing the compounds and methods for prevention or treatment of PPAR alpha mediated diseases or conditions.

Several independent risk factors have been associated with cardiovascular disease. These include hypertension, increased fibrinogen levels, high levels of triglycerides, elevated LDL cholesterol, elevated total cholesterol, and low levels of HDL cholesterol. HMG CoA reductase inhibitors ("statins") are useful for treating conditions characterized by high LDL-c levels. It has been shown that lowering LDL-c is not sufficient for reducing the risk of cardiovascular disease in some patients, particularly those with normal LDL-c levels. This population pool is identified by the independent risk factor of low HDL-c. The increased risk of cardiovascular disease associated with low HDL-c levels has not yet been successfully addressed by drug therapy (i.e., currently there are no drugs on the market that are useful for raising HDL-c >40%). (Bisgaier, C. L.; Pape, M. E. *Curr. Pharm. Des.* 1998, 4, 53–70).

Syndrome X (including metabolic syndrome) is loosely defined as a collection of abnormalities including hyperinsulinemia, obesity, elevated levels of trigycerdes, uric acid, fibrinogen, small dense LDL-c particles, and plasminogen activator inhibitor 1 (PAI-1), and decreased levels of HDL-c.

NIDDM is described as insulin resistance which in turn causes anomalous glucose output and a decrease in glucose uptake by skeletal muscle. These factors eventually lead to impaired glucose tolerance (IGT) and hyperinsulinemia.

Peroxisome Proliferator Activated Receptors (PPARs) are orphan receptors belonging to the steroid/retinoid receptor superfamily of ligand-activated transcription factors. See, for example, Willson, T. M. and Wahli, W., *Curr. Opin. Chem. Biol.*, (1997), Vol. 1, pp 235–241.

Three mammalian Peroxisome Proliferator-Activated Receptors have been isolated and termed PPAR-alpha, PPAR-gamma, and PPAR-delta (also known as NUC1 or PPAR-beta). These PPARs regulate expression of target genes by binding to DNA sequence elements, termed PPAR response elements (PPRE). To date, PPRE's have been identified in the enhancers of a number of genes encoding proteins that regulate lipid metabolism suggesting that PPARs play a pivotal role in the adipogenic signaling cascade and lipid homeostasis (H. Keller and W. Wahli, *Trends Endoodn. Met* 291–296, 4 (1993)).

Certain compounds that activate or otherwise interact with one or more of the PPARs have been implicated in the regulation of triglyceride and cholesterol levels in animal models. See, for example, U.S. Pat. No. 5,847,008 (Doebber et al.) and U.S. Pat. No. 5,859,051 (Adams et al.) and PCT publications WO 97/28149 (Leibowitz et al.) and WO99/04815 (Shimokawa et al.).

DETAILED DESCRIPTION OF THE INVENTION

Fibrates are a class of drugs which may lower serum triglycerides 20–50%, lower LDL-c 10–15%, shift the LDL particle size from the more atherogenic small dense to normal dense LDL-c, and increase HDL-c 10–15%. Experimental evidence indicates that the effects of fibrates on serum lipids are mediated through activation of PPAR alpha. See, for example, B. Staels et al., *Curr. Pharm. Des.*, 1–14, 3 (1), (1997). Activation of PPAR alpha results in transcription of enzymes that increase fatty acid catabolism and decrease de-novo fatty acid synthesis in the liver resulting in decreased triglyceride synthesis and VLDL-c production/secretion. In addition, PPAR alpha activation decreases production of apoC-III. Reduction in apoC-III, an inhibitor of LPL activity, increases clearance of VLDL-c. See, for example, J. Auwerx et al., *Atherosclerosis*, (Shannon, Irel), S29–S37, 124 (Suppl), (1996). PPAR alpha ligands may be useful for the treatment of dyslipidemia and cardiovascular disorders, see Fruchart, J. C., Duriez, P., and Staels, B., *Curr. Opin. Lipidol.* (1999), Vol 10, pp 245–257.

According to a first aspect of the invention there is provided a compound of formula (I) and pharmaceutically acceptable salts, solvates and hydrolysable esters thereof:

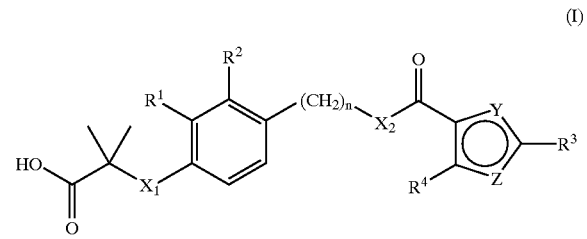

(I)

wherein;

$X_1$ represents O or S;

$R^1$ and $R^2$ independently represent H, halogen, —$CH_3$ and —$OCH_3$;

n represents 1 or 2;

$X_2$ represents NH, NCH, or O;

One of Y and Z is N, and the other is O or S;

$R^3$ represents phenyl or pyridyl (wherein the N is in position 2 or 3) and is optionally substituted by one or more halogen, $NO_2$, $NH_2$, $CF_3$, $OCF_3$, $OC_{1-6}$ straight or branched alkyl, $C_{1-6}$ straight or branched alkyl, alkenyl or alkynyl with the provision that when $R^3$ is pyridyl, the N is unsubstituted;

$R^4$ represents $CF_3$ or $CH_3$.

In another aspect, the present invention discloses a method for prevention or treatment of a human PPAR alpha ("hPPAR alpha") mediated disease or condition comprising administration of a therapeutically effective amount of a compound of this invention. hPPAR alpha mediated diseases or conditions include dyslipidemia including associated diabetic dyslipidemia and mixed dyslipidemia, syndrome X (as defined in this application this embraces metabolic syndrome), heart failure, hypercholesteremia, cardiovascular disease including atherosclerosis, arteriosclerosis, and hypertriglyceridemia, type II diabetes mellitus, type I diabetes, insulin resistance, hyperlipidemia, and regulation of appetite and food intake in subjects suffering from disorders such as obesity, anorexia bulimia, and anorexia nervosa. Other diseases or conditions include inflammation. In particular, the compounds of this invention are useful in the treatment and prevention of cardiovascular diseases and conditions including atherosclerosis, arteriosclerosis, hypertriglyceridemia, and mixed dyslipidaemia.

In another aspect, the present invention provides pharmaceutical compositions comprising a compound of the invention, preferably in association with a pharmaceutically acceptable diluent or carrier.

In another aspect, the present invention provides a compound of the invention for use in therapy, and in particular, in human medicine.

In another aspect, the present invention provides the use of a compound of the invention for the manufacture of a medicament for the treatment of a hPPAR alpha mediated disease or condition.

In another aspect, the present invention provides a method of treatment of a patient suffering from a hPPAR alpha mediated disease or condition comprising the administration of a therapeutically effective amount of a compound of the invention.

As used herein, "a compound of the invention" means a compound of formula (I) or a pharmaceutically acceptable salt, solvate, or hydrolyzable ester thereof.

While hydrolyzable esters are included in the scope of this invention, the acids are preferred because the data suggests that while the esters are useful compounds, it may actually be the acids to which they hydrolyze that are the active compounds. Esters that hydrolyze readily can produce the carboxylic acid in the assay conditions or in vivo. Generally the carboxylic acid is active in both the binding and transient transfection assays, while the ester does not usually bind well but is active in the transient transfection assay presumably due to hydrolysis. Preferred hydrolysable esters are $C_{1-6}$ alkyl esters wherein the alkyl group may be straight chain or branched chain. Methyl or ethyl esters are more preferred.

Preferably $X_1$ represents O.

Preferably one of $R^1$ and $R^2$ represents H with $R^1$ and $R^2$ both representing H being more preferred.

Preferably n represents 1.

Preferably $X_2$ represents NH.

Preferably Z represents N.

Preferably Y represents S.

Preferably $R^3$ is phenyl, optionally substituted. Preferably $R^3$ is mono or disubstituted. Preferably when $R^3$ is pyridyl the N is in the 2 position. $R^3$ preferably is monosubstituted in the para position and is more preferably phenyl. A preferred substituent is $CF_3$.

Preferably $R^4$ represents $CH_3$.

While the preferred groups for each variable have generally been listed above separately for each variable, preferred compounds of this invention include those in which several or each variable in Formula (I) is selected from the preferred, more preferred, or most preferred groups for each variable. Therefore, this invention is intended to include all combinations of preferred, more preferred, and most preferred groups.

Preferably, the compounds of formula (I) are hPPAR alpha agonists. As used herein, by "agonist", or "activating compound", or "activator", or the like, is meant those compounds which have a pKi of at least 6.0 to the relevant PPAR, for example hPPAR alpha, in the binding assay described below, and which achieve at least 50% activation of the relevant PPAR relative to the appropriate indicated positive control in the transfection assay described below at concentrations of $10^{-5}$ M or less. More preferably, the compounds of this invention achieve 50% activation of human PPAR alpha in the transfection assay at concentrations of $10^{-7}$ M or less.

Most preferably, the compounds of formula (I) are selective hPPAR alpha agonists. As used herein, a "selective hPPAR alpha agonist" is a hPPAR alpha agonist whose $EC_{50}$ for PPAR alpha is at least 10 fold lower than its $EC_{50}$ for PPAR gamma and PPAR delta. Such selective compounds may be referred to as "10-fold selective." $EC_{50}$ is defined in the transfection assay described below and is the concentration at which a compound achieves 50% of its maximum activity. Most preferred compounds are greater than 100-fold selective hPPAR alpha agonists.

Preferred compounds of the invention include:

2-methyl-2-[4-{[(4-methyl-2-[4-(fluoromethylphenyl]-thiazol-5-ylcarbonyl)amino]ethyl}phenoxy]propionic acid ethyl ester N-methyl-2-methyl-2-[4-{[(4-methyl-2-[4-trifluoromethylphenyl]-thiazol-5-ylcarbonyl)amino]ethyl}phenoxy]propionic acid ethyl ester 4-methyl-2-[4-trifluoromethylphenyl]-thiazol-5-carboxylic acid 4-(1-tertbutyloxycarbonyl-1-methylethoxy) benzyl ester 2-methyl-2-[4-{[(4-methyl-2-[4-tertbutylphenyl]-thiazol-5-ylcarbonyl)amino]methyl}phenoxy]propionic acid ethyl ester 2-methyl-2-[4-{[(4-methyl-2-[4-isopropylphenyl]-thiazol-5-ylcarbonyl)amino]methyl}phenoxy]propionic acid ethyl ester 2-methyl-2-[4-{[(4-methyl-2-[4-nitrophenyl]-thiazol-5-ylcarbonyl)amino]methyl}phenoxy]propionic acid ethyl ester 2-methyl-2-[4-{[(4-methyl-2-[4-aminophenyl]-thiazol-5-ylcarbonyl)amino]methyl}phenoxy]propionic acid ethyl ester 2-methyl-2-[4-{[(4-methyl-2-[4-aminophenyl]-thiazol-5-ylcarbonyl)amino]methyl}phenoxy]propionic acid 2-methyl-2-[4-{[(4-methyl-2-[3,4-dichlorophenyl]-thiazol-5-ylcarbonyl)amino]methyl}phenoxy] propionic acid ethyl ester 2-methyl-2-[4-{[(4-methyl-2-[3-fluorotrifluoromethylphenyl]-thiazol-5-ylcarbonyl)amino]methyl}phenoxy]propionic acid ethyl ester 2-methyl-2-[4-{[(4-methyl-2-[4-bromophenyl]-thiazol-5-ylcarbonyl)amino]methyl}phenoxy]propionic acid ethyl ester 2-methyl-2-[4-{[(4-methyl-2-[4-ethylphenyl]-thiazol-5-ylcarbonyl)amino]methyl}phenoxy]propionic acid ethyl ester 2-methyl-2-[4-{[(4-methyl-2-phenylthiazol-5-ylcarbonyl)amino]-methyl}phenoxy]propionic acid ethyl ester 2-methyl-2-[4-{[(4-methyl-2-[4-fluorophenyl]-thiazol-5-ylcarbonyl)amino]methyl}phenoxy]propionic acid ethyl ester 2-methyl-2-[4-{[(4-methyl-2-[4-chlorophenyl]-thiazol-5-ylcarbonyl)amino]methyl}phenoxy]propionic acid ethyl ester 2-methyl-2-[4-{[(4-methyl-2-[4-trifluoromethoxyphenyl]-thiazol-5-ylcarbonyl)amino] methyl}phenoxy]propionic acid ethyl ester 2-methyl-2-[4-{[(4-methyl-2-[4-methoxyphenyl]-thiazol-5-ylcarbonyl)amino]methyl}phenoxy]propionic acid ethyl ester 2-methyl-2-[4-{[(4-methyl-2-[4-acetylenylphenyl]-thiazol-5-ylcarbonyl)amino]methyl}phenoxy] propionic acid ethyl ester 2-methyl-2-[4-{[(4-trifluoromethyl-2-[4-trifluoromethylphenyl]-thiazol-5-ylcarbonyl)amino]methyl}phenoxy]propionic acid ethyl ester 2-methyl-2-[4-{[(4-trifuoromethyl-2-[4-tertbutylphenyl]-thiazol-5-ylcarbonyl)amino]methyl}phenoxy] propionic acid ethyl ester 2-methyl-2-[4-{[(4-trifluoromethyl-2-[4-tertbutylphenyl]-thiazol-5-ylcarbonyl)amino]methyl}phenoxy]propionic acid 2-methyl-2-[4-{[(4-methyl-2-[4-trifluromethylphenyl]-oxazol-5-ylcarbonyl)amino]methyl}phenoxy] propionic acid ethyl ester 2-methyl-2-[4-{[(4-methyl-2-[4-trifluromethyl-2-pyridyl]-thiazol-5-ylcarbonyl)amino]methyl}phenoxy] propionic acid ethyl ester 2-methyl-2-[2-methoxy-4-{[(4-methyl-2-[4-trifluromethylphenyl]-thiazol-5-ylcarbonyl)amino] methyl}phenoxy]propionic acid ethyl ester 2-methyl-2-[2-methyl-4-{[(4-methyl-2-[4-trifluromethylphenyl]-thiazol-5-ylcarbonyl)amino] methyl}phenoxy]propionic acid ethyl ester 2-methyl-2-[2-methyl-4-{[(4-methyl-2-[4-trifluromethylphenyl]-thiazol-5-ylcarbonyl)amino] methyl}phenoxy]propionic acid 2-methyl-2-[2-methyl-4-{[(4-methyl-2-[4-isopropylphenyl]-thiazol-5-ylcarbonyl)amino] methyl}phenoxy]propionic acid ethyl ester 2-methyl-2-[2-methyl-4-{[(4-methyl-2-[4-isopropylphenyl]-thiazol-5-ylcarbonyl)amino] methyl}phenoxy]propionic acid 2-methyl-2-[4-{[(5-methyl-2-[4-trifluoromethylphenyl]-thiazol-4-ylcarbonyl)amino]methyl}phenoxy] propionic acid ethyl ester 2-methyl-2-[4-{[(5-methyl-2-[4-trifluoromethylphenyl]-thiazol-4-ylcarbonyl)amino]methyl}phenoxy] propionic acid 2-methyl-2-[4-{[(5-methyl-2-[3-trifluoromethylphenyl]-thiazol-4-ylcarbonyl)amino]methyl}phenoxy] propionic acid ethyl ester 2-methyl-2-[4-{[(5-methyl-2-[3-trifluoromethylphenyl]-thiazol-4-ylcarbonyl)amino]methyl}phenoxy] propionic acid More preferred compounds of the invention include:

2-methyl-2-[4-{[(4-methyl-2-[4-trifluoromethylphenyl]-thiazol-5-ylcarbonyl)amino]ethyl}phenoxy]propionic acid ethyl ester 2-methyl-2-[4-{[(4-methyl-2-[4-trifluoromethylphenyl]-thiazol-5-ylcarbonyl)amino]ethyl}phenoxy]propionic acid N-methyl-2-methyl-2-[4-{[(4-methyl-2-[4-trifluoromethylphenyl]-thiazol-5-ylcarbonyl)amino] ethyl}phenoxy]propionic acid 2-methyl-2-[4-{[(4-methyl-2-[4-tertbutylphenyl]-thiazol-5-ylcarbonyl)amino]methyl}phenoxy]propionic acid 2-methyl-2-[4-{[(4-methyl-2-[4-isopropylphenyl]-thiazol-5-ylcarbonyl)amino]methyl}phenoxy] propionic acid 2-methyl-2-[4-{[(4-methyl-2-[4-nitrophenyl]-thiazol-5-ylcarbonyl)amino]methyl}phenoxy]propionic acid 2-methyl-2-[4-{[(4-methyl-2-[3,4-dichlorophenyl]-thiazol-5-ylcarbonyl)amino]methyl}phenoxy] propionic acid 2-methyl-2-[4-{[(4-methyl-2-[3-fluorotrifluoromethylphenyl]-thiazol-5-ylcarbonyl) amino]methyl}phenoxy]propionic acid 2-methyl-2-[4-{[(4-methyl-2-[4-bromophenyl]-thiazol-5-ylcarbonyl)amino]methyl}phenoxy]propionic acid 2-methyl-2-[4-{[(4-methyl-2-[4-ethylphenyl]-thiazol-5-ylcarbonyl)amino]methyl}phenoxy]propionic acid 2-methyl-2-[4-{[(4-methyl-2-phenylthiazol-5-ylcarbonyl)amino]methyl}phenoxy]propionic acid 2-methyl-2-[4-{[(4-methyl-2-[4-fluorophenyl]-thiazol-5-ylcarbonyl)amino]methyl}phenoxy]propionic acid 2-methyl-2-[4-{[(4-methyl-2-[4-chlorophenyl]-thiazol-5-ylcarbonyl)amino]methyl}phenoxy]propionic acid 2-methyl-2-[4-{[(4-methyl-2-[4-trifluoromethoxyphenyl] thiazol-5-ylcarbonyl)amino]methyl}phenoxy] propionic acid 2-methyl-2-[4-{[(4-methyl-2-[4-methoxyphenyl]-thiazol-5-ylcarbonyl)amino]methyl}phenoxy]propionic acid 2-methyl-2-[4-{[(4-methyl-2-[4-acetylenylphenyl]-thiazol-5-ylcarbonyl)amino]methyl}phenoxy] propionic acid 2-methyl-2-[4-{[(4-trifluoromethyl-2-[4-trifluoromethylphenyl]-thiazol-5-ylcarbonyl)amino] methyl}phenoxy]propionic acid 2-methyl-2-[4-{[(4-methyl-2-[4-trifluromethylphenyl]-oxazol-5-ylcarbonyl)amino]methyl}phenoxy] propionic acid 2-methyl-2-[4-{[(4-methyl-2-[4-trifluromethyl-2-pyridyl]-thiazol-5-ylcarbonyl)amino]methyl}phenoxy] propionic acid 2-methyl-2-[2-methoxy-4-{[(4-methyl-2-[4-trifluromethylphenyl]-thiazol-5-ylcarbonyl)amino] methyl}phenoxy]propionic acid A particularly preferred compound of the invention is 2-methyl-2-[4-{[(4-methyl-2-[trifluoromethylphenyl]thiazol-5-yl-carbonyl)amino]methyl}phenoxy]propionic acid.

The preferred compound listed above is a selective hPPAR alpha agonist.

It will also be appreciated by those skilled in the art that the compounds of the present invention may also be utilized in the form of a pharmaceutically acceptable salt or solvate thereof. The physiologically acceptable salts of the compounds of formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'- dibeenzylethylenediamine, chloroprocaine, choline, diethanolamine, ethylenediamine, N-methylglucamine and procaine salts. References hereinafter to a compound according to the invention include both compounds of formula (I) and their pharmaceutically acceptable salts and solvates.

The compounds of the invention and their pharmaceutically acceptable derivatives are conveniently administered in the form of pharmaceutical compositions. Such compositions may conveniently be presented for use in conventional manner in admixture with one or more physiologically acceptable carriers or excipients.

While it is possible that compounds of the present invention may be therapeutically administered as the raw chemical, it is preferable to present the active ingredient as a pharmaceutical formulation. The carrier(s) must be "acceptable" in the sense of being compatible with the other ingredients of the formulation and not deleterious to the recipient thereof.

Accordingly, the present invention further provides for a pharmaceutical formulation comprising a compound of formula (I) or a pharmaceutically acceptable salt or solvate thereof together with one or more pharmaceutically acceptable carriers therefore and, optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy. All methods include the step of bringing into association the compounds ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic add. Such preparations may also be formulated as suppositories, e.g., containing conventional suppository bases such as cocoa butter or other glycerides.

Formulations for parenteral administration include aqueous and non-aqueous sterile injection solutions which may contain anti-oxidants, buffers, bacterostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freezeried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated by those skilled in the art that reference herein to treatment extends to prophylaxis as well as the treatment of established diseases or symptoms.

Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 1–1500 mg per day. The desired dose may conveniently be presented in a single dose or as divided doses administered at appropriate intervals, for example as two, three, four or more sub-doses per day. The formulations according to the invention may contain between 0.1–99% of the active ingredient, conveniently from 30–95% for tablets and capsules and 3–50% for liquid preparations.

The compound of formula (I) for use in the instant invention may be used in combination with other therapeutic agents for example, statins and/or other lipid lowering drugs for example MTP inhibitors and LDLR upregulators. The compounds of the invention may also be used in combination with antidiabetic agents, e.g. metformin, sulfonylureas and/or PPAR gamma agonists (for example thiazolidinediones such as e.g. Pioglitazone and Rosiglitazone). The compounds may also be used in combination with antihypertensive agents such as calcium channel antagonists and ACE inhibitors. The invention thus provides in a further aspect the use of a combination comprising a compound of formula (I) with a further therapeutic agent in the treatment of a hPPAR alpha mediated disease.

When the compounds of formula (I) are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optimally together with a pharmaceutically acceptable carrier or excipient comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, conveniently in such a manner as are known for such compounds in the art.

When a compound of formula (I) is used in combination with a second therapeutic agent active against the same hPPAR alpha mediated disease, the dose of each compound may differ from that when the compound is used alone. Appropriate doses will be readily appreciated by those skilled in the art.

Compounds of this invention may be conveniently prepared by a general process wherein a moiety like (A) is coupled to an acid (B) using a peptide coupling reaction or by alkylation of (A) using a suitable non nucleophilic amine with an acid chloride (C). Preferably, R is 1–6 alkyl which can be hydrolyzed off to give an acid of Formula (I), or if readily hydrolyzable, the resulting ester can be administered.

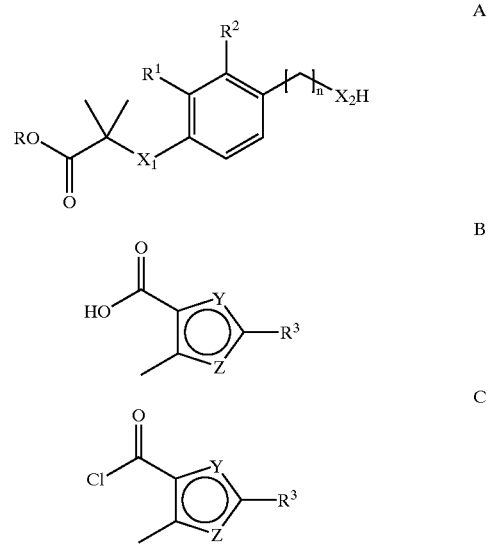

A preferred synthesis of (A) when $X_1$ is O and $X_2$ is NH (and $R^1$ and $R^2$ are H) is:

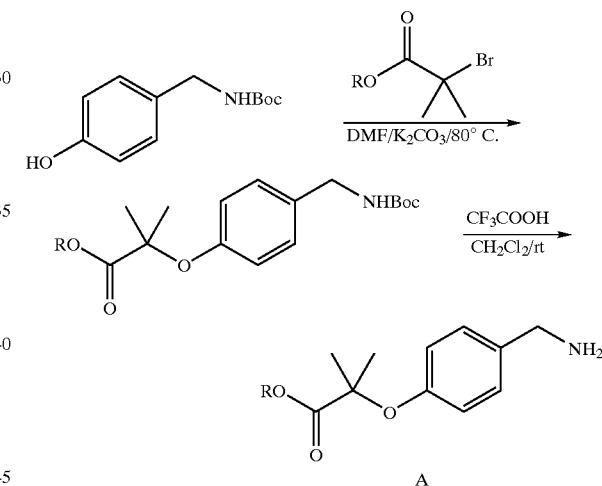

Note that this synthesis is preferably carried out with the amine where the alcohol function is already alkylated with the acid side chain protected by R. For example, when n is 1, $X_1$ is O, $X_2$ is NH, Y is S, Z is N, $R^1$ and $R^2$ are H, and $R^3$ is 4-$F_3$C-phenyl:

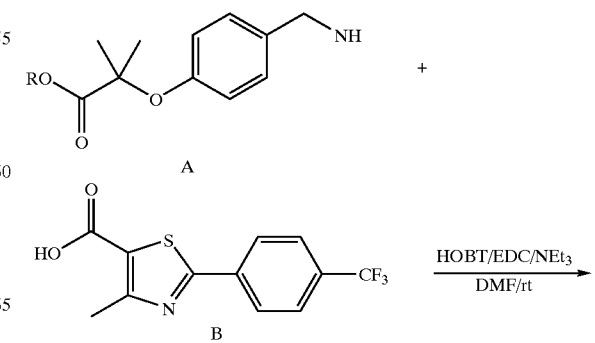

-continued

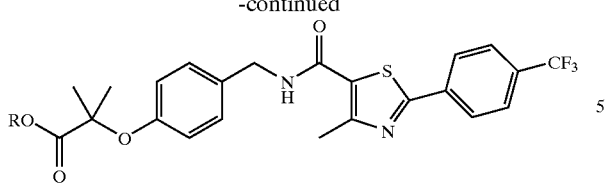

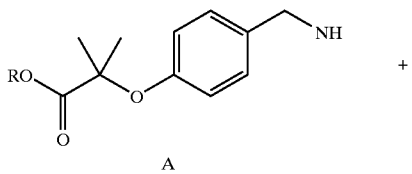

A

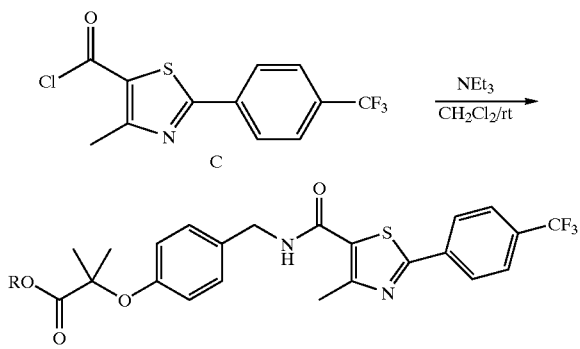

Some of the intermediates of type A are commercially available while others can be synthesized by techniques apparent to a person skilled in the art. The synthesis of intermediates of type B and C are illustrated below.

Compounds of the invention may be made by an alternative method in which compounds of formula (D) are reacted with ethyl 2-bromo-2 methyl propionate to produce the ethyl ester of the compound of formula (I) which may be hydrolysed to produce the free acid.

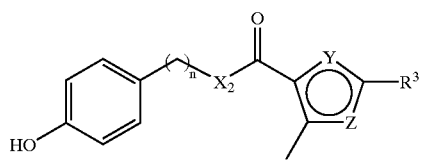

D

Compounds of formula (D) may be prepared from the reaction between compounds of formula (B) and compounds of formula (E) with HOBT/EDC/NEt$_3$ when X$_2$ is NH or NCH$_3$ or DIC/DMAP/NEt$_3$ when X$_2$ is O.

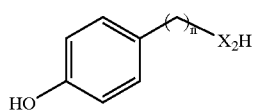

E

The invention is further illustrated by the following examples which should not be construed as constituting a limitation thereto.

Intermediate 1

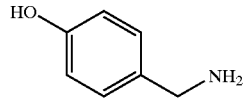

The procedure was as described in Stout, D. M. *J. Med. Chem.* 1983, 26(6), 808–13. To 4-methoxybenzyl amine (25 g, 0.18 mol; Aldrich) was added 46% HBr in H$_2$O (106 ml, 0.9 mol; Aldrich). The reaction was refluxed overnight, then the reaction cooled to 0° C. and neutralized to pH7 slowly with KOH$_{(s)}$. The reaction was allowed to stir for ~30 min, then the solid filtered and dried. The solid was redissolved in hot MeOH, filtered and the solution cooled to afford 19 g (85%) intermediate 1. $^1$H NMR (DMSO-d$_6$): δ 8.0 (bs, 1H), 7.2 (d, 2H), 6.75 (d, 2H), 3.85 (s, 2H), 3.50 (bs, 2H).

Intermediate 2

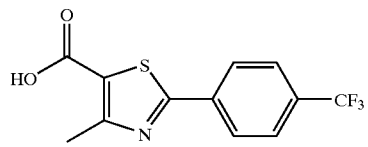

A solution of ethyl 2-chloroacetoacetate (35.3 g, 29.7 mL, 0.21 mol) and 4-(trifluoromethyl)thiobenzamide (44 g, 0.21 mol) in EtOH (300 mL) was refluxed overnight. After cooling to room temperature the solvent was removed in vacuo. The final product (intermediate 2) was recrystallized from a minimum of MeOH to afford 40 g (59%) of final product as a white solid. $^1$H NMR (CDCl$_3$): δ 8.10 (d, 2H), 7.70 (d, 2H), 4.40 (q, 2H), 2.80 (s, 3H), 1.4 (t, 3H).

Intermediate 3

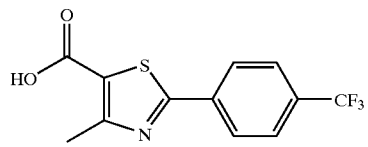

To intermediate 2 (1.84 g, 5.8 mmol) in THF was added 1 N LiOH (6 mL, 6 mmol) and the reaction stirred at rt. After ~3 h, the reaction was neutralized with 1N HCl, extracted 3×100 mL EtOAc, dried over Na$_2$SO$_4$, filtered and the solvent removed under vacuum to afford 1.5 g (89%) intermediate 3 as a white solid. $^1$H NMR (DMSO-d$_6$): δ 13.55 (bs, 1H), 8.25 (d, 2H), 7.95 (d, 2H), 2.75 (s, 3H).

Intermediate 4

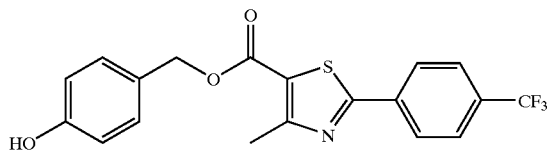

To intermediate 3 (1 g, 7 mmol) in CH$_2$Cl$_2$/DMF (1:1) was added HOBT (565 mg, 4.2 mmol; Aldrich), EDC (800 mg, 4.2 mmol; Aldrich) and intermediate 1 (860 mg, 7 mmol). The reaction was stirred at rt for 18 h. The solvent was removed in vacuo, treated with H$_2$O and extracted 3×100 mL CH$_2$Cl$_2$. The organic phases combined and washed with 1N HCl, dried over Na$_2$SO$_4$, filtered and evaporated to afford a mixture (N-substituted and N,O-substituted). The mixture was dissolved in MeOH and treated with 1N NaOH. The reaction was stirred 18 h at 50° C. The solvent was removed in vacuo, and the residue was dissolved in CH$_2$Cl$_2$, washed with H$_2$O, and dried over Na$_2$SO$_4$. The solvent was evaporated and the residue chromatographed (CH$_2$Cl$_2$/MeOH: 99/1) to afford 610 mg (47%) of intermediate 4 as a white solid. $^1$H NMR (DMSO-d$_6$): δ 9.30 (s, 1H), 8.80 (t, 1H), 8.20 (d, 2H), 6.70 (d, 2H), 4.35 (d, 2H), 2.6 (s, 3H).

General Procedure 1 for the Preparation of Substituted Thiobenzamides

To a solution of P$_4$S$_{10}$ (0.2 mmol) in toluene (100 mL) was added NaHCO$_3$ (2 mmol) and the mixture heated to reflux for ca. 30 min. The substituted benzamide (1 mmol) was added and the reaction stirred at 90° C. for 1 h. The reaction was then evaporated to dryness, treated with brine (100 mL) and extracted with CH$_2$Cl$_2$ (2×50 mL). The organic phase dried, filtered, and evaporated to afford the final product.

Intermediate 5

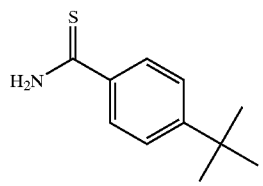

The title compound was prepared as described in general procedure 1 to afford an orange solid (49%). $^1$H NMR (CDCl$_3$): δ 7.7 (d, 2H), 7.4 (bs, 1H), 7.3 (d, 2H), 7.0 (bs, 1H), 1.2 (s, 9H).

Intermediate 6

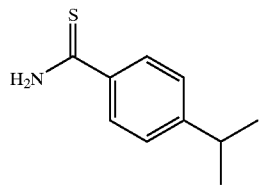

The title compound was prepared as described in general procedure 1 to afford an orange solid (26%).
Mp: 150° C.

General Procedure 2 for the Preparation of Substituted Thiobenzamides

To the substituted benzonitrile (1 mmol) in DMF (30 mL) is added dropwise DMF (21 mL) saturated with HCl$_{(g)}$ during 1 min. Thioacetamide (2 mmol) is then added and the reaction heated to 100° C. for 1 h. HCl$_{(g)}$ is bubbled in for ca. 1 min and the stirring continued at 100° C. for another 18 h. The reaction cooled to rt, treated with ice and extracted with Et$_2$O (3×250 mL). The organic phase was washed with H$_2$O (3×300 mL), dried over Na$_2$SO$_4$, filtered, and evaporated to dryness. The residue was washed with a mixture of isopropyl ether/pentane (1:3) to afford the final product.

Intermediate 7

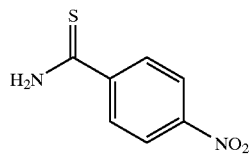

The title compound was prepared as described in general procedure 2 to afford an orange solid (83%). $^1$H NMR (DMSO-d$_6$): δ 10.1 (bs, 1H), 9.7 (bs, 1H), 8.1 (d, 2H), 7.9 (d, 2H).

Intermediate 8

The title compound was prepared as described in general procedure 2 to afford a yellow solid (45%).
MS m/z 207 (M+1).

Intermediate 9

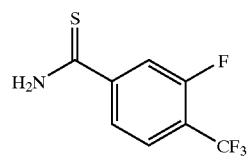

The title compound was prepared as described in general procedure 2 to afford an orange solid (84%). $^1$H NMR (DMSO-d$_6$): δ 10.5 (bs, 1H), 10.05 (bs, 1H), 8.1 (m, 3H).

Intermediate 10

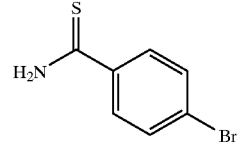

To 4-bromobenzonitrile (1 mmol) was added the diethyldithiophosphate (1.2 equiv.). To the suspension was added H$_2$O (ca. 100 mL) and the reaction heated to 80° C. for ca. 2 h. The reaction cooled to rt and extracted with Et$_2$O (3×100 mL). The organic phase was washed with sat. NaHCO$_3$, dried over NaSO$_4$ and evaporated to dryness leaving a yellow solid. The solid was rinsed with isopropyl ether and collected by filtration to afford the title compound as a yellow solid (55%).
MS m/z 214.

Intermediate 11

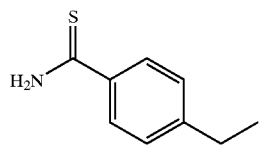

To the 4-ethylbenzamide (1 mmol) in toluene heated to reflux, was added Laweson's reagent (1 equiv.). After the addidition was complete, the reaction was refluxed for 2 h. The reaction cooled to rt, treated with $Et_2O$, washed with $H_2O$ and the organic phase dried over $Na_2SO_4$. The solution filtered, evaporated to dryness and the residue chromatographed with $CH_2Cl_2$/MeOH (98:2) to afford 3 g of the title compound as a yellow solid (55%). $^1H$ NMR (DMSO-$d_6$): δ 9.8 (bs, 1H), 9.4 (bs, 1H), 7.8 (d, 2H), 7.2 (d, 2H), 2.6 (q, 2H), 1.2 (t, 3H).

General Procedure 3 for the Preparation of 2-Substituted Phenyl-4-methyl-1,3-thiazole-5-caboxylic Acid Ethyl Esters To a solution of the substituted thiobenzamide (1 mmol) in EtOH (100 mL) was added ethyl 2-chloroacetoacetate (1.1 mmol) and the mixture heated to reflux overnight. The reaction is cooled to room temperature and the solvent evaporated. The solid is crystallized from $Et_2O$ or hexane to afford the final product.

Intermediate 12

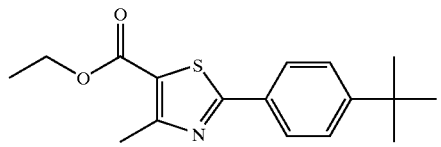

Intermediate 5 was reacted as described in general procedure 3 to afford the title compound as an off-white solid (95%). $^1H$ NMR ($CDCl_3$): δ 8.0 (d, 2H), 7.55 (d, 2H), 4.45 (q, 2H), 3.85 (s, 3H), 2.5 (t, 3H), 1.45 (s, 9H).

Intermediate 13

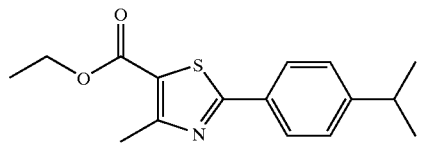

Intermediate 6 was reacted as described in general procedure 3 to afford the title compound as an off-white solid (97%). $^1H$ NMR ($CDCl_3$): δ 7.85 (d, 2H), 7.25 (d, 2H), 4.30 (q, 2H), 2.90 (st, 1H), 2.70 (s, 3H), 1.30 (t, 3H), 1.20 (d, 6H).

Intermediate 14

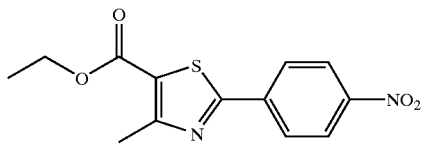

Intermediate 7 was reacted as described in general procedure 3 to afford the title compound as an yellow solid (74%). $^1H$ NMR ($CDCl_3$): δ 8.25 (d, 2H), 8.05 (d, 2H), 4.30 (q, 2H), 2.70 (s, 3H), 1.30 (t, 3H).

Intermediate 15

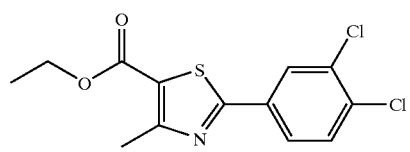

Intermediate 8 was reacted as described in general procedure 3 to afford the title compound as an pale yellow solid (77%). $^1H$ NMR ($CDCl_3$): δ 8.0 (d, 1H), 7.70 (dd, 1H), 7.40 (d, 1H), 4.30 (q, 2H), 2.70 (s, 3H), 1.3 (s, 3H).

Intermediate 16

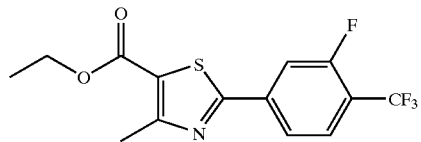

Intermediate 9 was reacted as described in general procedure 3 to afford the title compound as an off-white solid (40%). $^1H$ NMR (DMSO-$d_6$): δ 7.95 (m, 3H), 4.30 (q, 2H), 2.65 (s, 3H), 1.3 (s, 3H).

Intermediate 17

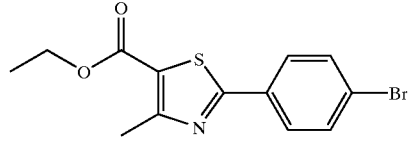

Intermediate 10 was reacted as described in general procedure 3 to afford the title compound as an off-white solid (61%). $^1H$ NMR ($CDCl_3$): δ 7.70 (d, 2H), 7.55 (d, 2H), 4.25 (q, 2H), 2.70 (s, 3H), 1.30 (s, 3H).

Intermediate 18

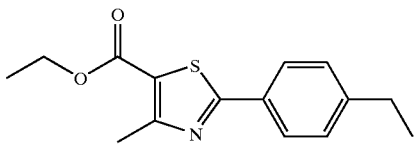

Intermediate 11 was reacted as described in general procedure 3 to afford the title compound as a pale green solid (35%). $^1$H NMR (CDCl$_3$): δ 7.70 (d, 2H), 7.15 (d, 2H), 4.15 (q, 2H), 2.50 (s, 3H), 2.50 (q, 2H), 1.15 (t, 3H), 1.05 (t, 3H).

Intermediate 19

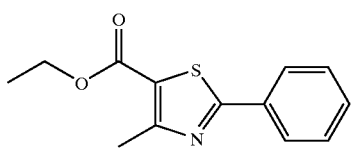

The thiobenzamide (Aldrich) was reacted as described in general procedure 3 to afford the title compound as an off-white solid (28%). $^1$H NMR (CDCl$_3$): δ 8.35 (d, 2H), 7.60 (m, 3H), 4.45 (q, 2H), 3.05 (s, 3H), 1.30 (t, 3H).

Intermediate 20

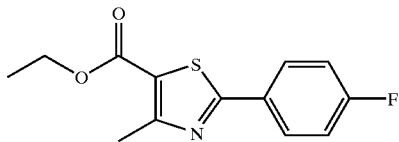

The 4-fluorothiobenzamide (Maybridge) was reacted as described in general procedure 3 to afford the title compound as an off-white solid (100%). $^1$H NMR (CDCl$_3$): δ 7.75 (dd, 2H), 6.95 (t, 2H), 4.15 (q, 2H), 2.60 (s, 3H), 1.20 (t, 3H).

Intermediate 21

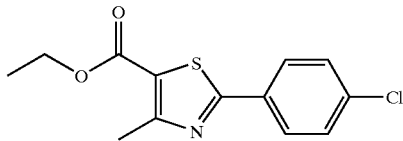

The 4-chlorothiobenzamide (Lancaster) was reacted as described in general procedure 3 to afford the title compound as an pale orange solid (54%). $^1$H NMR (CDCl$_3$): δ 7.60 (d, 2H), 7.10 (d, 2H), 4.15 (q, 2H), 2.55 (s, 3H), 1.20 (t, 3H).

Intermediate 22

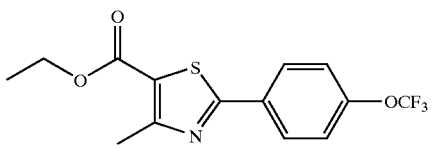

The 4-trifluoromethoxythiobenzamide (Interchim) was reacted as described in general procedure 3 to afford the title compound as an off-white solid (100%). $^1$H NMR (CDCl$_3$): δ 7.90 (d, 2H), 7.15 (d, 2H), 4.25 (q, 2H), 2.65 (s, 3H), 1.30 (t, 3H).

Intermediate 23

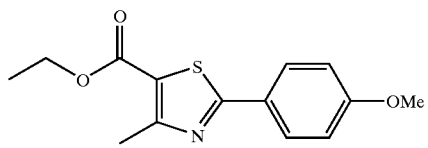

The 4-methoxythiobenzamide (Lancaster) was reacted as described in general procedure 3 to afford the title compound as an off-white solid (52%). $^1$H NMR (DMSO-d$_6$): δ 7.8 (d, 2H), 6.95 (d, 2H), 4.15 (q, 2H), 3.70 (s, 3H), 2.50 (s, 3H), 1.15 (t, 3H).

General Procedure 4 for the Preparation of 2-Substituted Phenyl-4-methyl-1,3-thiazole-5-caboxylic Acids To a solution of the substituted thiazole ester (1 mmol) in EtOH (100 mL) was added (1.5 equiv.) NaOH (1N) and the mixture heated to 40° C. overnight. The reaction is cooled to room temperature and the solution acidified with HCl (1N). The precipitate is collected washed with H$_2$O and dried under vaccum to afford the final product.

Intermediate 24

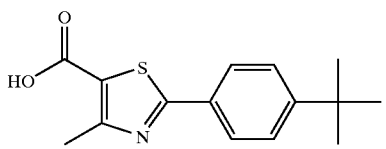

Intermediate 12 was reacted as described in general procedure 4 to afford the title compound as an off-white solid (64%). $^1$H NMR (CDCl$_3$): δ 7.70 (d, 2H), 7.30 (d, 2H), 2.60 (t, 3H), 1.15 (s, 9H).

Intermediate 25

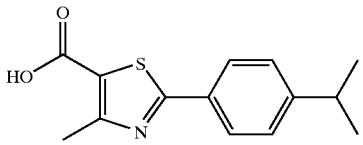

Intermediate 13 was reacted as described in general procedure 4 to afford the title compound as an off-white solid (100%). ¹H NMR (CDCl₃): δ 7.75 (d, 2H), 7.15 (d, 2H), 2.85 (st, 1H), 2.65 (s, 3H), 1.15 (d, 6H).

Intermediate 26

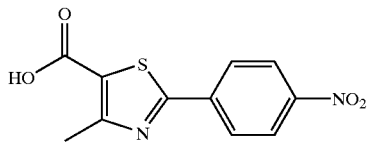

Intermediate 14 was reacted as described in general procedure 4 to afford the title compound as a beige solid (99%). ¹H NMR (DMSO-d₆): δ 8.15 (d, 2H), 8.05 (d, 2H), 2.50 (s, 3H).

Intermediate 27

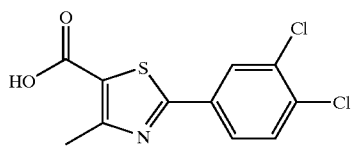

Intermediate 15 was reacted as described in general procedure 4 to afford the title compound as an off-white solid (91%). ¹H NMR (DMSO-d₆): δ 8.35 (d, 1H), 8.05 (dd, 1H), 7.90 (d, 1H), 2.80 (s, 3H).

Intermediate 28

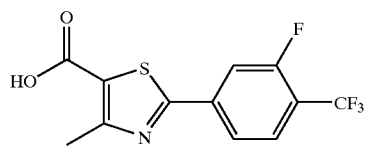

Intermediate 16 was reacted as described in general procedure 4 to afford the title compound as an off-white solid (82%). ¹H NMR (DMSO-d₆): δ 8.05 (m, 3H), 2.75 (s, 3H).

Intermediate 29

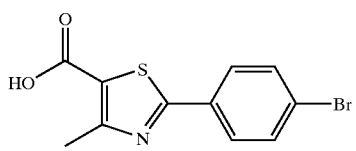

Intermediate 17 was reacted as described in general procedure 4 to afford the title compound as an off-white solid (87%). ¹H NMR (DMSO-d₆): δ 7.70 (d, 2H), 7.45 (d, 2H), 2.45 (s, 3H).

Intermediate 30

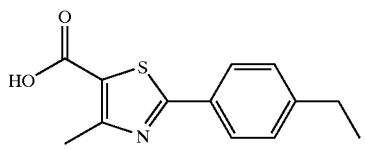

Intermediate 18 was reacted as described in general procedure 4 to afford the title compound as a pale green solid (79%). ¹H NMR (DMSO-d₆): δ 8.05 (d, 2H), 7.50 (d, 2H), 2.75 (q, 2H), 2.75 (s, 3H), 1.30 (t, 3H).

Intermediate 31

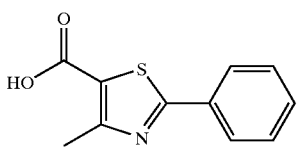

Intermediate 19 was reacted as described in general procedure 4 to afford the title compound as an off-white solid (93%).

Mp 215° C.

Intermediate 32

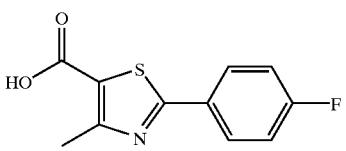

Intermediate 20 was reacted as described in general procedure 4 to afford the title compound as an off-white solid (85%). ¹H NMR (DMSO-d₆): δ 8.0 (dd, 2H), 7.30 (t, 2H), 2.60 (s, 3H).

Intermediate 33

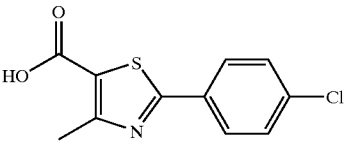

Intermediate 21 was reacted as described in general procedure 4 to afford the title compound as an pale orange solid (92%). ¹H NMR (DMSO-d₆): δ 7.95 (d, 2H), 7.55 (d, 2H), 2.60 (s, 3H).

Intermediate 34

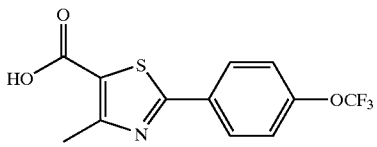

Intermediate 22 was reacted as described in general procedure 4 to afford the title compound as an off-white solid (66%).
MS m/z 304 (M+1).

Intermediate 35

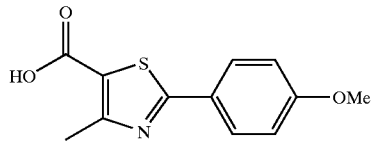

Intermediate 23 was reacted as described in general procedure 3 to afford the title compound as an off-white solid (98%). $^1$H NMR (DMSO-d$_6$): δ 7.95 (d, 2H), 7.10 (d, 2H), 3.90 (s, 3H), 2.70 (s, 3H).

Intermediate 36

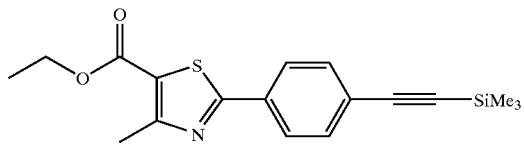

Intermediate 17 (1 mmol) was diluted in a mixture of MeCN/dioxane (100 mL) then CuI (0.05 equiv.) and 1,1,3,3-tertamethylguanidine (10 equiv.) was added and the reaction stirred 15 min under a N$_2$ atmosphere. The reaction purged under vaccum and then trimethylsilylacetylene (1.1 equiv.) and Pd(PPh$_3$)$_2$Cl$_2$ (0.1 equiv.) added and the reaction stirred at 80° C. for 2 h. The solvent evaporated, the residue dissolved in CH$_2$Cl$_2$, washed with sat. NH$_4$Cl, then NH$_4$OH and finally brine. The organic layer dried over Na$_2$SO$_4$, filtered and evaporated. The crude product was chromatographed eluting with CH$_2$Cl$_2$ to afford the title compound as a beige solid (100%).
MS m/z 344 (M+1).

Intermediate 37

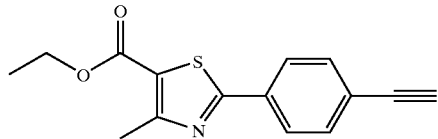

To intermediate 36 (1 mmol) in THF was added Bu$_4$NF and the reaction stirred at rt for 2 h. The THF was evaporated, the residue dissolved in CH$_2$Cl$_2$, washed with sat. NH$_4$Cl, then NH$_4$OH and finally brine. The organic layer dried over Na$_2$SO$_4$, filtered and evaporated. The crude product was chromatographed eluting with CH$_2$Cl$_2$ to afford the title compound as white solid (44%).
MS m/z 272 (M+1).

Intermediate 38

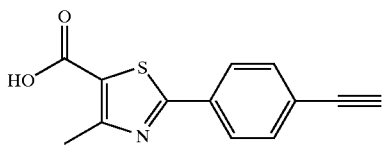

Intermediate 37 was reacted as described in general procedure 4 to afford the title compound as a pale yellow solid (79%).
MS m/z 244 (M+1).

Intermediate 39

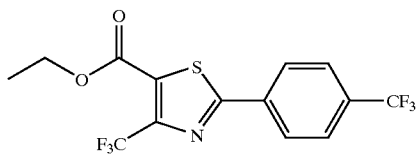

To the 4-trifluoromethylthiobenzamide (1 equiv., Lancaster) in DMF (150 mL) was added ethyl 2-chloro-4,4,4-trifluoroacetoacetate (1.5 equiv., Lancaster) and the reaction stirred at 100° C. for 18 h. The reaction is cooled, concentrated and the residue chromatographed eluting with CH$_2$Cl$_2$. The yellow oil that is collected is titrated with hexane to afford the title compound as a white solid (13%).
MS m/z 369.

Intermediate 40

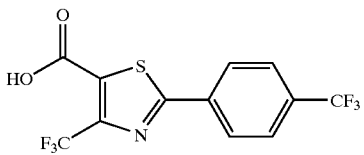

Intermediate 39 was reacted as described in general procedure 4 to afford the title compound as a white solid (94%). $^1$H NMR (DMSO-d$_6$): δ 8.1 (d, 2H), 7.7 (d, 2H).

Intermediate 41

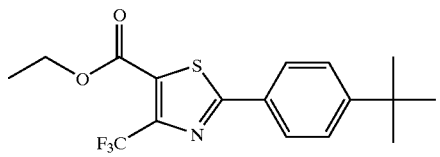

To intermediate 5 (1 equiv.) in EtOH (25 mL) was added ethyl 2-chloro-4,4,4-trifluoroacetoacetate (1 equiv., Lancaster) and the reaction stirred at reflux for 91 h. The reaction is cooled, concentrated, the residue dissolved in pentane and filtered. The solvent removed under vaccum to afford the title compound as a brown oil containing 2 compounds which was used without further purification

Intermediate 42

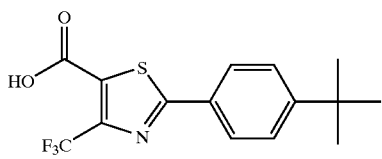

Intermediate 41 was reacted as described in general procedure 4 to afford the title compound as a mixture of 2 compounds. The mixture was chromatographed with cyclohexane/ethyl acetate (7/3) to recover the impurity then with $CH_2Cl_2$/MeOH (98/2) to recover the title compound as a white solid (9.7%).

MS m/z 329 (M+1).

Intermediate 43

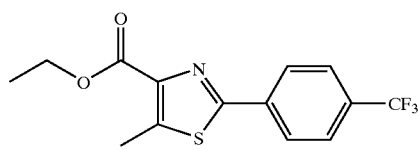

To the 4-trifluoromethylthiobenzamide (1 equiv., Lancaster) in EtOH (100 mL) was added the ethyl 3-bromo-2-oxobutyrate (1.1 equiv.) and the reaction stirred at reflux for 18 h. The reaction cooled to rt, concentrated and the residue dissolved in $CH_2Cl_2$. The organic layer was washed with sat. $NaHCO_3$ followed by $H_2O$, dried over $Na_2HCO_4$, filtered and the solvent evaporated to dryness; The crude product was chromatographed eluting with $CH_2Cl_2$ to afford the title compound as a white solid (60%).

Intermediate 44

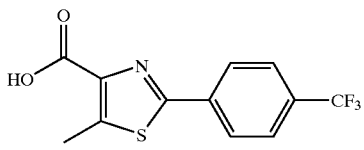

Intermediate 43 was reacted as described in general procedure 4 to afford the title compound as a white solid (74%).

MS m/z 287.

Intermediate 45

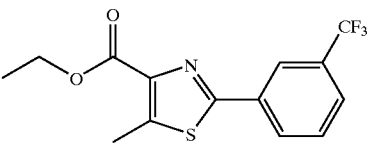

To the 3-trifluoromethylthiobenzamide (1 equiv., Lancaster) in EtOH (100 mL) was added the ethyl 3-bromo-2-oxobutyrate (1.1 equiv.) and the reaction stirred at reflux for 18 h. The reaction cooled to rt, concentrated and the residue dissolved in $CH_2Cl_2$. The organic layer was washed with sat. $NaHCO_3$ followed by $H_2O$, dried over $Na_2HCO_4$, filtered and the solvent evaporated to dryness; The crude product was chromatographed eluting with $CH_2Cl_2$ to afford the title compound as a yellow oil (81%).

MS m/z 315.

Intermediate 46

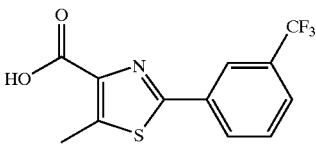

Intermediate 45 was reacted as described in general procedure 3 to afford the title compound as a white solid (92%).

MS m/z 288 (M+1).

Intermediate 47

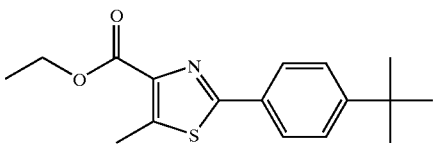

Intermediate 5 (1 equiv.) in EtOH (100 mL) was added the ethyl 3-bromo-2-oxobutyrate (1.1 equiv.) and the reaction stirred at reflux for 18 h. The reaction cooled to rt, concentrated and the residue dissolved in $CH_2Cl_2$. The organic layer was washed with sat $NaHCO_3$ followed by $H_2O$, dried over $Na_2HCO_4$, filtered and the solvent evaporated to dryness; The crude product was chromatographed eluting with $CH_2Cl_2$ to afford the title compound as a pale yellow solid (56%).

Mp 108° C.

Intermediate 48

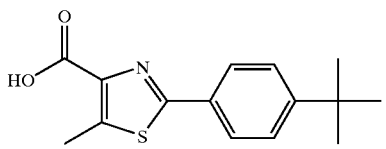

Intermediate 47 was reacted as described in general procedure 4 to afford the title compound as a pale yellow solid (99%).

Mp 155° C.

Intermediate 49

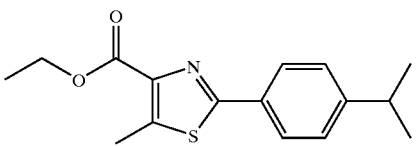

Intermediate 6 (1 equiv.) in EtOH (100 mL) was added the ethyl 3-bromo-2-oxobutyrate (1.1 equiv.) and the reaction stirred at reflux for 18 h. The reaction cooled to rt, concentrated and the residue dissolved in CH$_2$Cl$_2$. The organic layer was washed with sat. NaHCO$_3$ followed by H$_2$O, dried over Na$_2$HCO$_4$, filtered and the solvent evaporated to dryness; The crude product was chromatographed eluting with CH$_2$Cl$_2$ to afford the title compound as a yellow oil (48%).

MS m/z 289.

Intermediate 50

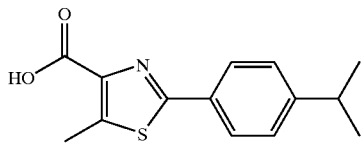

Intermediate 49 was reacted as described in general procedure 4 to afford the title compound as a white solid (73%).

MS m/z 262 (M+1).

Intermediate 51

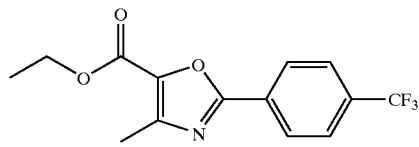

To 4-(trifluoromethyl)benzamide (1 equiv.) in toluene (150 mL) was added droppwise the methyl 3-bromo-2-oxobutyrate (1 equiv.) and the reaction stirred at reflux for 20 h. The reaction was diluted with EtOAc (100 mL) and succesively washed with: NaOH (1N), HCl (1N) and water (3×100 mL), dried, filtered and evaporated to a syrup. The resulting mixture was purified by flash column chromatography [CH$_2$Cl$_2$ then CH$_2$Cl$_2$/MeOH (99.5:0.5)] to afford the title compound as a white solid (9%).

MS m/z 285.

Intermediate 52

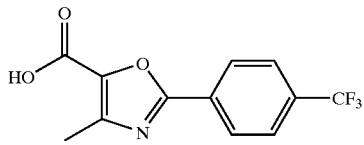

Intermediate 51 was reacted as described in general procedure 4 to afford the title compound as a white solid (86%).

Mp 189.

Intermediate 53

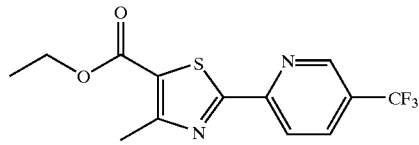

(4-trifluoromethyl-2-pyridyl)thioamide (Lancaster) was reacted as described in general procedure 3 to afford the title compound as a white solid (48%).

Intermediate 54

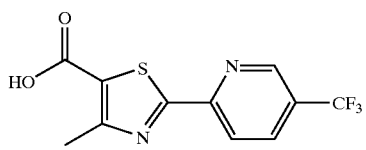

Intermediate 53 was reacted as described in general procedure 4 to afford the title compound as a grey solid (84%). $^1$H NMR (DMSO-d$_6$): δ 9.13 (d, 1H), 8.43 (dd, 1H), 8.35 (d, 1H), 2.75 (s, 3H).

Intermediate 55

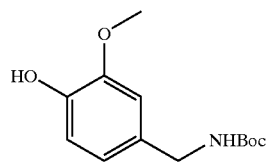

To 4-hydroxy-3-methoxybenzylamine hydrochloride (1 equiv., Aldrich) in CH$_2$Cl$_2$ (300 mL) at 0° C. was added Et$_3$N (3 equiv.). Boc anhydride (0.95 equiv) in CH$_2$Cl$_2$ (50 mL) was added dropwise. The reaction was allowed to warm to rt and stirring continued for 18 h. The reaction was then poured into NaOH (1N) and the mixture extracted with NaOH (3×50 mL). The aqueous phases combined, acidified with HCl (1N) and extracted with CH$_2$Cl$_2$ (3×100 mL). The organic layers washed with H$_2$O, dried over Na$_2$SO$_4$, filtered and the solvent removed under vaccum to afford the title compound as a clear oil (97%). $^1$H NMR (CDCl$_3$): δ 6.75 (m, 3H), 5.55 (bs, 1H), 4.75 (bs, 1H), 4.15 (d, 2H), 3.80 (s, 3H), 1.40 (s, 9H).

Intermediate 56

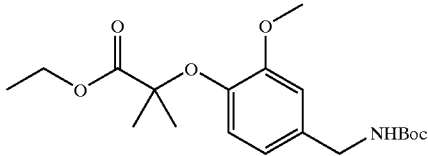

To intermediate 56 (1 equiv.) in DMSO (100 mL) was added K$_2$CO$_3$ (3 equiv.) and ethyl 2-bromo-2-methylproprionate (1.3 equiv.). The reaction was stirred while heating at 100° C. for 3 h. The reaction was poured onto ice and extracted with CH$_2$Cl$_2$ (3×50 mL). The combined organic layers were washed with NaOH (1N), then H$_2$O and dried over Na$_2$SO$_4$. The solution filtered, evaporated to dryness and the crude product cristallized from hot hexane to afford the title compound as a brown solid (63%).

Mp 107–109° C.

Intermediate 57

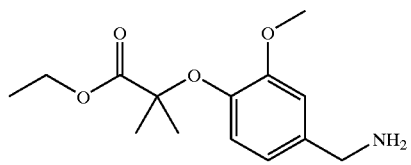

To intermediate 56 (1 equiv.) in CH$_2$Cl$_2$ (10 mL) at rt was added droppwise CF$_3$COOH (7 equiv.) and the reaction stirred at rt for 18 h. The reaction was evaporated to dryness, treated with a sat. K$_2$CO$_3$ solution and extracted with CH$_2$Cl$_2$ (3×150 mL). The combined organic layers were dried over Na$_2$SO$_4$, filtered and evaporated to dryness to afford the title compound as an oil (100%).

MS m/z 267.

Intermediate 58

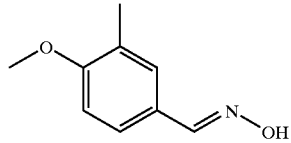

To 4-methoxy-3-methylbenzalehyde (1 equiv., Acros) in EtOH (150 mL) at rt was added H$_2$NOH,HCl (1.6 equiv.), (3 equiv.) NaOAc in 150 mL H$_2$O and the reaction stirred for 2 h. The EtOH was evaporated, and the residue extracted with CH$_2$Cl$_2$ (3×50 mL). The combined organic layers were washed with H$_2$O, dried over Na$_2$SO$_4$, filtered and evaporated to dryness to afford the title compound as a white solid (93%).

Mp 71–73° C.

Intermediate 59

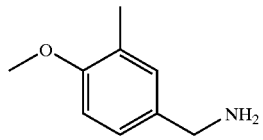

To intermediate 58 (1 equiv.) in MeOH (200 mL) at rt was added [MeCO$_2$]NH$_4$ (6 equiv.), Pd/C (0.01 equiv.) and molecular sieves. The reaction was then heated to reflux for 18 h. The reaction was filtered through celite, evaporated to dryness and treated with HCl (1N). The aqueous layer was washed with CH$_2$Cl$_2$, filtered, basified to pH>14 and extracted with CH$_2$Cl$_2$ (3×50 mL). The combined organic layers were washed with H$_2$O, dried over Na$_2$SO$_4$, filtered and evaporated to dryness to afford the title compound as an oil (46%).

MS m/z 151.

Intermediate 60

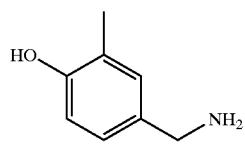

Intermediate 59 (1 equiv.) in excess 40% HBr/H$_2$O (Aldrich) was refluxed for 18 h. The reaction was then evaporated to dryness to afford the title compound hydrobromide salt as a grey solid (97%).

Mp 235–237° C.

Intermediate 61

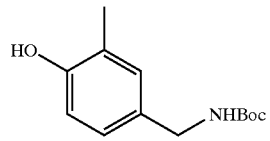

To Intermediate 60 (1 equiv.) in CH$_2$Cl$_2$ (300 mL) at 0° C. was added Et$_3$N (3 equiv.). Boc anhydride (0.95 equiv.) in CH$_2$Cl$_2$ (50 mL) was added dropwise. The reaction was allowed to warm to rt and stirring continued for 18 h. HCl (1N) was added and the reaction extracted with CH$_2$Cl$_2$ (3×100 mL). The organic layers washed with H$_2$O, dried over Na$_2$SO$_4$, filtered and the solvent removed under vaccum to afford the title compound as a white solid (96%).

Mp 105–107° C.

Intermediate 62

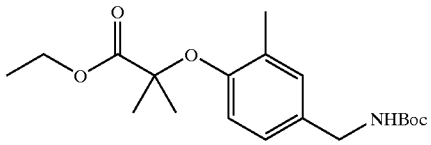

To intermediate 61 (1 equiv.) in DMF (150 mL) was added K$_2$CO$_3$ (3 equiv.) and the reaction heated to 70° C. Ethyl 2-bromo-2-methylproprionate (1.3 equiv.) was added droppwise and the reaction was stirred for 72 h at 70° C. The reaction was poured onto ice and extracted with CH$_2$Cl$_2$ (3×150 mL). The combined organic layers were washed with NaOH (0.5N), then H$_2$O and dried over Na$_2$SO$_4$. The solution filtered, evaporated to dryness to afford the title compound as an oil (69%). $^1$H NMR (CDCl$_3$): δ 7.05 (d, 1H), 6.90 (dd, 1H), 6.60 (d, 1H), 4.80 (bs, 1H), 4.25 (q, 2H), 4.20 (d, 2H), 2.20 (s, 3H), 1.60 (s, 6H), 1.45 (s, 9H), 1.25 (t, 3H).

Intermediate 63

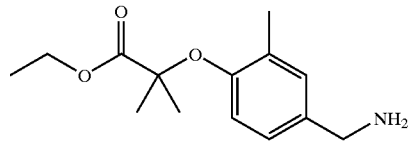

To intermediate 62 (1 equiv.) in CH$_2$Cl$_2$ (10 mL) at rt was added dropwise CF$_3$COOH (7 equiv.) and the reaction stirred at rt for 18 h. The reaction was evaporated to dryness, treated with a sat. K₂CO₃ solution and extracted with CH₂Cl₂ (3×150 mL). The combined organic layers were dried over Na₂SO₄, filtered and evaporated to dryness to afford the title compound as an oil (82%). ¹H NMR (CDCl₃): δ 7.00 (d, 1H), 6.90 (dd, 1H), 6.55 (d, 1H), 4.20 (q, 2H), 3.70 (s, 2H), 2.15 (s, 3H), 1.85 (bs, 2H), 1.50 (s, 6H), 1.20 (t, 3H).

Intermediate 64

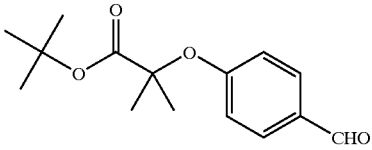

To 4-hydroxybenzaldehyde (1 equiv.) in DMF (150 mL) was added NaH (1.5 equiv.) and the reaction stirred at 80° C. for 30 min. Ethyl 2-bromo-2-methylproprionate (1.2 equiv.) was added dropwise and the reaction was stirred for 24 h at 80° C. The reaction was evaporated to dryness, the residue treated with NaOH and extracted with CH₂Cl₂ (5×100 mL). The combined organic layers were dried over Na₂SO₄, filtered and the solvent evaporated to to afford crude intermediate 64. After chromatography eluting with CH₂Cl₂/MeOH (98:2) the title compound was obtained as an oil (20%). ¹H NMR (CDCl₃): δ 9.80 (s, 1H), 7.75 (d, 2H), 6.80 (d, 2H), 1.55 (s, 6H), 1.3 (s, 9H).

Intermediate 65

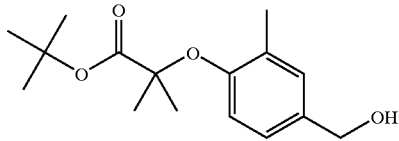

To intermediate 64 (1 equiv.) in MeOH (50 mL) at rt was added NaBH₄ (1 equiv.) and the reaction stirred at rt while it was followed by tlc [CH₂Cl₂/MeOH (98:2); Rf=0.45]. When all the starting material had disappeared, the solvent was evaporated to dryness, the residue treated with H₂O and extracted with CH₂Cl₂ (3×50 mL). The combined organic layers were dried over Na₂SO₄, filtered and evaporated to dryness to afford the title compound as a semi-solid (100%). ¹H NMR (CDCl₃): δ 7.20 (d, 2H), 6.80 (d, 2H), 4.55 (s, 2H), 1.50 (s, 6H), 1.35 (s, 9H).

Intermediate 66

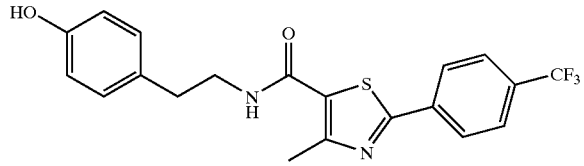

To the 4-hydroxyphenethyl amine (1 equiv.) in DMF (75 mL) at rt was added HOBT (1.1 equiv.), EDC (1.1 equiv.) and Et₃N (1.5 equiv.). To the mixture was added dropwise intermediate 3 in DMF and the reaction was stirred at rt for 18 h. The reaction was evaporated to dryness, treated with a HCl (1N) and extracted with EtOAc (3×150 mL). The combined organic layers were dried over Na₂SO₄, filtered and evaporated to dryness. The crude intermediate 66 was chromatogaphed eluting with CH₂Cl₂/MeOH (9:1) to afford the title compound as a white solid (64%). ¹H NMR (CDCl₃): δ 9.2 (s, 1H), 8.40 (t, 3H), 8.10 (d, 2H), 7.85 (d, 2H), 7.05 (d, 2H), 6.70 (d, 2H), 3.40 (m, 2H), 2.70 (m, 2H), 2.60 (s, 3H).

EXAMPLE 1

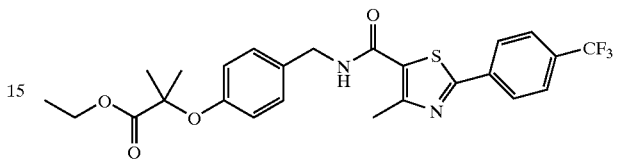

2-Methyl-2-[4-{[(4-methyl-2-[4-trifluoromethylphenyl]thiazol-5-ylcarbonyl)amino]methyl}phenoxy]propionic Acid Ethyl Ester To intermediate 4 (710 mg, 1.81 mmol) in DMF (50 mL) was added the K₂CO₃ (275 mg, 1.99 mmol) followed by the ethyl 2-bromo-2-methylpropanoate (280 μL, 1.91 mmol; Aldrich) and the reaction heated to 80° C. After 18 h, the reaction was cooled to rt and the solvent removed in vacuo. The residue was treated with water (200 mL), extracted 3×50 mL CH₂Cl₂, dried over Na₂SO₄, filtered and the solvent removed under vacuum. The residue was chromatographed (CH₂Cl₂/MeOH: 99/1) to afford 680 mg (77%) of example 1 as a clear oil. ¹H NMR(CDCl₃): δ 7.95 (d, 2H), 7.60 (d, 2H), 7.15 (d, 2H), 6.75 (d, 2H), 6.05 (t, 1H), 4.45 (d, 2H), 4.15 (q, 2H), 2.65 (s, 3H), 1.50 (s, 6H), 1.20 (t, 3H).

EXAMPLE 2

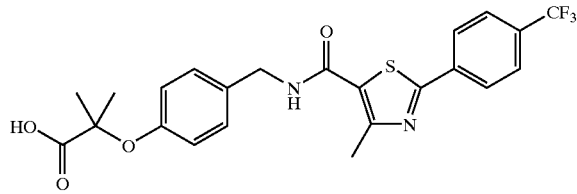

2-Methyl-2-[4-{[(4-methyl-2-[4-trifluoromethylphenyl]-thiazol-5-ylcarbonyl)amino]methyl}phenoxy]propionic Acid To Example 1 (680 mg, 1.39 mmol) in MeOH was added 1N NaOH (1.6 mL, 1.6 mmol) and the reaction stirred at 60° C. After 18 h, the reaction cooled to rt and the solvent evaporated. The residue was treated with 1N HCl, extracted 3×20 mL THF and the solvent removed under vacuum. 500 mg (75%). The title compound was precipitated as a white solid from a minimum volume of CH₂Cl₂ and pentane. mp: changes form between 60–70° C.; LC/MS (m/z): 477.22 (100%, AP−), 479.12 (100%, AP+); anal. C₂₃H₂₁F₃N₂O₄S: C, 5.71 (57.73), H, 4.56 (4.42), N, 5.77 (5.85), S, 6.15 (6.70).

An improved synthesis of 2-methyl-2-[4-{[(4-methyl-2-[4-trifluoromethylphenyl]-thiazol-5-ylcarbonyl)amino]methyl}phenoxy]-propionic acid is:

Intermediate 67

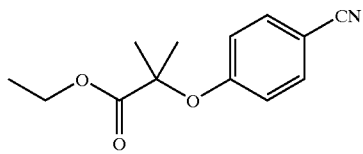

To a solution of 212.8 g (1.79 moles) of para hydroxybenzonitrile in 1.7 L of DMF (8 vol.) cooled to 15° C. were added portionwise 121 g (3.04 mol., 1.7 equiv.) of NaH dispersed in parafin (60%) in 35 minutes. After return to room temperature, the mixture was stirred for 30 minutes and 393 mL (2.68 mol., 1.5 equiv.) of ethyl bromoisobutyrate were slowly added in 1 hour. During the addition, the inert temperature was maintained below 25° C. by cooling because a slightly exothermic effect occurred. The mixture was stirred overnight at room temperature and heated at 80° C. for 2 hours. After cooling at a temperature below 20° C., the excess of sodium hydride was destroyed by the addition of 600 ml of 1N sodium hydroxide solution. The aqueous solution was extracted 3 times with 1L of ethyl ether. The combined organic layers were washed twice with 200 ml of 1N sodium hydroxide solution (to eliminate traces of the para hydroxybenzonitrile) and 500 ml of brine. After drying on magnesium sulphate, filtered and concentrated to dryness, the oily residue was decanted and 33.5 g of the parafin oil was removed (the upper layer). The 189.9 g of the oily residue was estimate to be mixed with 14.9 g of residual parafin oil. Crude intermediate 67 was used without further purification. The yield is estimated to be about 42% (about 175 g).

Intermediate 68

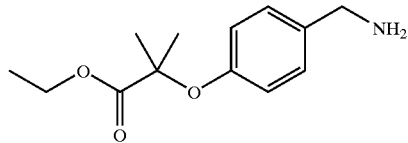

In a hydrogenator of 1 L, a mixture of 59.3 g of intermediate 67 (0.254 mol. (maximum), 43.6 ml (0.762 mol., 3 equiv.) of glacial acetic acid and 6 g (10% w/w) of Pd/C 10% in 250 ml of ethyl alcohol was hydrogenated over 2 bars of hydrogen and at room temperature. The reaction stopped after 8 hours when 8.7 L of hydrogen were absorbed (theoretical volume: 11.4 L). After filtration of the catalyst, the solution was evaporated to dryness to give the acetic salt of intermediate 68 (oily residue). The residue was poured in 300 ml of water (pH=5) and the aqueous layer was extracted twice with 200 ml of cyclohexane. During this operation, a gummy solid appeared which is left in the aqueous layer (probably a part of the acetic salt). After addition of 400 ml of ethyl acetate, the biphasic mixture was cooled to 15° C. and treated with 500 ml of 1N NaOH solution (to pH=12). After decantation, the aqueous layer was extracted twice with 400 ml of ethyl acetate. The combined organic layer was washed with 200 ml of brine.

After drying on magnesium sulphate, the organic layer was filtered and concentrated to dryness to give 35.5 g of crude intermediate 68 (yellow oil, yield=58.9%) which were used in the next step without further purification (LC-MS purity=about 90%).

Intermediate 69

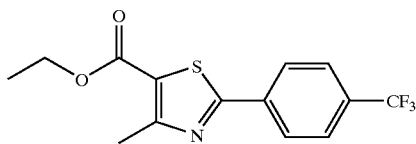

To a suspension of 302.4 g (1.47 mol.) of 4-(trifluoromethyl)thiobenzamide in 1.5 L (5 vol.) of ethyl alcohol were added at room temperature in one time 203.8 ml (1 equiv.) of ethyl 2-chloroacetoacetate. The solution was refluxed for 24 hours. The reaction was follow up by tlc (CH₂Cl₆) and hplc. After completion of the reaction, the solvent was removed under reduce pressure. The solid material was stirred with 500 ml of cooled hexane for 30 minutes, filtered and washed twice with 150 ml of hexane. After drying, 352.9 g of crude intermediate 69 were obtained. A second crop of 25.7 g was obtained by concentration of hexane to 50 ml. The overall yield was 81.5% (378.6 g).

Intermediate 70

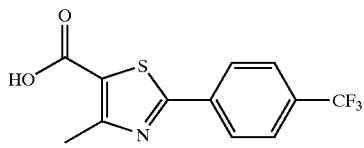

To a cooled solution of 378.6 g (1.2 mol.) of the intermediate 69 in 2 L (5 vol.) of ethyl alcohol were added 96.15 g (2 equiv.) of sodium hydroxide in 2 L of water. The solution was heated at 85° C. for 1.5 hours. After evaporation of the ethyl alcohol, the aqueous solution was diluted with 2 L of water and acidified to pH=1 with concentrated aqueous hydrochloric acid. The solid material was filtered, washed twice with 1 L of water and 1 L of dichloromethane. After drying in a vacuum oven, 267.2 g of an off-white powder were obtained. A second crop of 25.7 g was obtained by concentration of the dichloromethane and triturating with pentane. The overall yield was 85% (292.9 g).

EXAMPLE 3

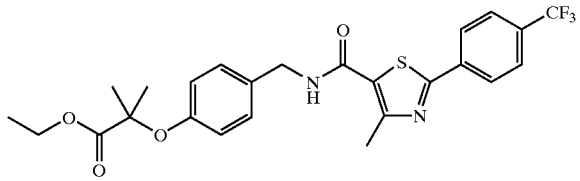

2-Methyl-2-[4-{[(4-methyl-2-[4-trifluoromethylphenyl]thiazol-5-ylcarbonyl)amino] methyl}phenoxy]propionic Acid Ethyl Ester A suspension of 38.7 g (0.13 mol.) of crude intermediate 70 in 200 ml (5 vol.) of thionyl chloride was refluxed for 3 hours. After return to room temperature, the thionyl chloride was removed under reduce pressure, the residue was twice suspended in toluene (100 ml) and evaporated to dryness. The crude acid chloride obtained (off-white solid) was used without purification. To a solution of 35.5 g (1 equiv./LC- MS purity: 90%) of crude intermediate 68 and 20.62 ml (1.1 equiv.) of triethylamine in 350 ml of dichloromethane (10 vol.) maintained at 10° C., was added portionwise the acid chloride in 20 minutes. The mixture was then stirred at room temperature overnight. The reaction was quenched by addition of 200 ml of water and stirring for 5 minutes. The biphasic mixture was decanted and the aqueous layer extracted twice with 200 ml of dichloromethane. The whole organic layer was washed respectively with 200 ml of hydrochloric acid (1N), 200 ml of water, 200 ml of saturated aqueous sodium carbonate and 200 ml of brine. After drying on magnesium sulphate, filtration and concentration to dryness, the crude material was suspended in 200 ml of isopropyl ether, triturated, filtered and dried to give 47.6 g of example 3 (white powder, yield=69.7%).

EXAMPLE 4

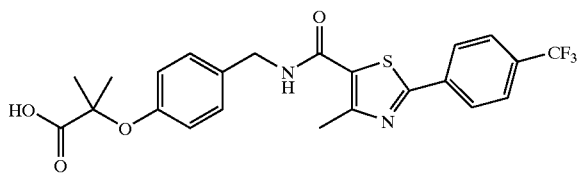

2-Methyl-2-[4-{[(4-methyl-2-[4-trifluoromethylphenyl]-thiazol-5-ylcarbonyl)amino]methyl}phenoxy]propionic Acid To a solution of 230.8 g (0.46 mol.) of example 3 in 1.2 L (5 vol.) of tetrahydrofuran were added 480 ml (1.05 equiv.) of aqueous sodium (1N). The solution was stirred at reflux for 18 hours. After removal of THF under reduced pressure, 500 ml of 1N NaOH and 100 ml of methyl alcohol were added. The aqueous layer was extracted twice with 400 ml of dichloromethane and acidified to pH=1 with concentrated aqueous hydrochloric acid. The oily residue was extracted with dichloromethane (3×400 ml). The whole organic layer was washed with 600 ml of brine. After drying on magnesium sulphate, filtration and concentration to dryness, the oily residue was organised with 500 ml of pentane, filtered, washed twice with 250 ml of pentane to give after drying 207.2 g of crude example 4 (white powder). The solid material was dissolved in 310 ml (1.5 vol.) of refluxed toluene. After filtration of the hot solution and return to room temperature, the crystallised material was filtered, washed twice with 200 ml of toluene and dried in vacuum oven to give 196.3 g of white powder of example 4 (yield=90%), mp=130–131° C., tlc (CH$_2$Cl$_2$/MeOH=9/1): monospot, hplc analysis: 99.5% (detection at 310 nm).

EXAMPLE 5

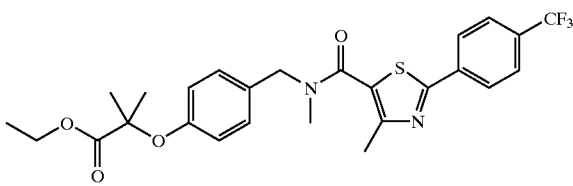

N-Methyl-2-methyl-2-[4-{[(4-methyl-2-[4-trifluoromethylphenyl]-thiazol-5-ylcarbonyl)amino]methyl}phenoxy]propionic Acid Ethyl Ester To a solution of example 4 (600 mg, 1.2 mmol.) in 50 mL of DMF was added 32 mg (1.1 equiv.) of NaH and the mixture stirred at 40° C. for 30 min. 85 µL (1.1 equiv.) of MeI was then added and the reaction as stirred at 40° C. for 18 h. After removal of DMF under reduced pressure, the residue was washed with H$_2$O and extracted with Et$_2$O (3×50 mL). The organic layer combined and dried over Na$_2$SO$_4$, filtered, evaporated to dryness and chromatographed with 100% CH$_2$Cl$_2$ then 99:1 CH$_2$Cl$_2$/MeOH to afford 300 mg of example 5 as a clear oil (yield=49%).

MS m/z 521 (M+1).

EXAMPLE 6

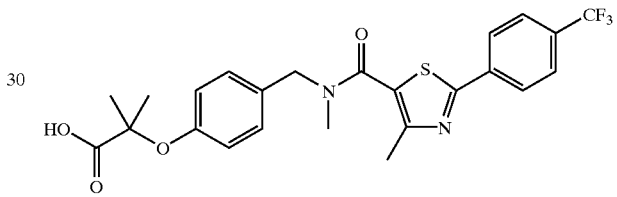

N-Methyl-2-methyl-2-[4-{[(4-methyl-2-[4-trifluoromethylphenyl]-thiazol-5-ylcarbonyl)amino]methyl}phenoxy]propionic Acid To a solution of example 6 (300 mg, 0.6 mmol) in 50 mL of EtOH was added 692 µL (1.2 equiv.) of NaOH (1N) and the mixture stirred at 60° C. for 18 h. After removal of EtOH under reduced pressure, the residue was treated with HCl and the solid collected, dried under vaccum and recrystalized from iPr$_2$O to afford 230 mg of example 6 as a white solid (yield=49%).

MS m/z 493 (M+1).

General Proceedure 5 for the Preparation of Salts of 2-Methyl-2-[4-{[(4-methyl-2-[4-trifluoromethylphenyl]-thiazol-5-ylcarbonyl)amino]methyl}phenoxy]propionic Acid At room temperature, to a solution of 500 mg of example 2 in 25 ml of acetonitrile was added 1 equivalent of the base*. After stirring for 3 or 24 hours*, the mixture was filtered and the solid material was washed with pentane and dried in a vacuum oven*. (*See table 1 of results below)

TABLE 1

|  | Base | Quantity Base | Stirring Time | Amounts of salt | Yield |
| --- | --- | --- | --- | --- | --- |
| Example 5 | NaOH (solution 1N) | 1.05 ml | 24 h | 0.37 g | 71% |
| Example 6 | N⁀OH | 58 µl | 3 h | 0.38 g | 68% |

TABLE 1-continued

| Base | Quantity Base | Stirring Time | Amounts of salt | Yield |
|---|---|---|---|---|
| Example 7 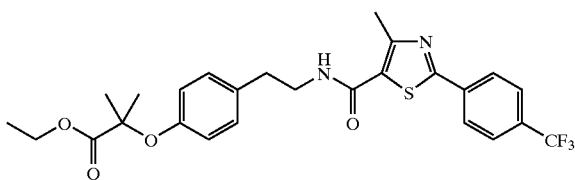 | 100.2 µl | 3 h | 0.55 g | 90% |
| Example 8 | 0.204 g | 24 h | 0.69 g | 98% |

(Example 8 base structure shown in table)

EXAMPLE 9

2-Methyl-2-[4-{[(4-methyl-2-[4-trifluoromethylphenyl]-thiazol-5-ylcarbonyl)amino]ethyl}phenoxy]propionic Acid Ethyl Ester To intermediate 66 (1 equiv.) in DMF (150 mL) was added $K_2CO_3$ (1.2 equiv.), ethyl 2bromo-2-methylpropionate (1.1 equiv.) and the reaction stirred at 80° C. for 18 h. The reaction was evaporated to dryness, the residue treated with NaOH (1N) and extracted with EtOAc (4×50 mL). The combined organic layers were dried over $Na_2SO_4$, filtered and the solvent evaporated to to afford crude example 9. After chromatography eluting with $CH_2Cl_2$/MeOH (95:5) the title compound was obtained as a white solid (86%). $^1H$ NMR ($CDCl_3$): δ 7.95 (d, 2H), 7.6 (d, 2H), 7.05 (d, 2H), 6.75 (d, 2H), 5.70 (t, 1H), 4.20 (q, 2H), 3.60 (m, 2H), 2.80 (m, 2H), 2.75 (s, 3H), 1.50 (s, 6H), 1.20 (t, 3H).

General Procedure 6 for the Peptide Coupling Reaction Between Intermediates of Type A and B To intermediate B (1 equiv.) in $CH_2Cl_2$ (75 mL) at rt was added HOBT (1.1 equiv.), EDC (1.1 equiv.) and $Et_3N$ (3 equiv.). To the mixture was added intermediate A and the reaction was stirred at rt for 18 h. The reaction was washed with HCl (1N), NaOH (1N) and 2×$H_2O$. The organic layer was dried over $Na_2SO_4$, filtered and evaporated to dryness. The crude compound was chromatogaphed or crystallized as necessary to afford the final product.

General Procedure 7 for the Alkylation Reaction Between Intermediates of Type A and C To intermediate B (1 equiv.) in toluene (25 mL) was added $SOCl_2$ and the reaction heated at 80° C. for 18 h. The reaction evaporated to dryness to afford the crude intermediate C which was redissolved in 10 mL toluene and re-evaporated to dryness. To intermediate A and $Et_3N$ (3 equiv.) in $CH_2Cl_2$ (50 mL) at rt was added intermediate C (1 equiv.) in $CH_2Cl_2$ and the reaction was stirred at rt for 3 h. The reaction was washed with HCl (1N), NaOH (1N) and $H_2O$. The organic layer was dried over $Na_2SO_4$, filtered and evaporated to dryness. The crude compound was chromatogaphed or recrystallized as necessary to afford the final product.

General Procedure 8 for the Hydrolysis of the Ethyl Esters

To a solution of the ethyl ester (1 mmol) in MeOH (50 mL) was added (3 equiv.) NaOH (1N) and the mixture heated to 60° C. overnight. The reaction is cooled to room temperature and the solution acidified with HCl (1N) and extracted with $CH_2Cl_2$ (3×25 mL). The combined organic layers washed with $H_2O$, dried over $Na_2SO_4$, filtered and evaporated to dryness. The solid was titrated with $Et_2O$, collected and dried under vaccum to afford the final product.

EXAMPLE 10

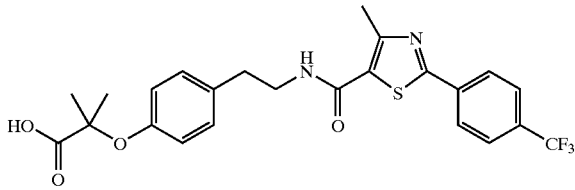

2-Methyl-2-[4-{[(4-methyl-2-[4-trifluoromethylphenyl]-thiazol-5-ylcarbonyl)amino]ethyl}phenoxy]propionic Acid Example 9 was reacted as described in general procedure 8 to afford the title compound as a white solid (74%). MS m/z 493 (M+1).

EXAMPLE 11

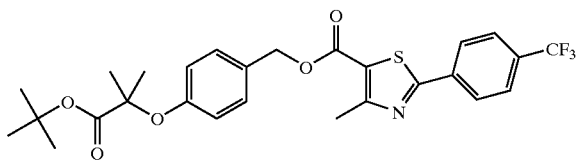

4-Methyl-2-[4-trifluoromethylphenyl]-thiazol-5-carboxylic Acid 4-(1-Tertbutyloxycarbonyl-1-methylethoxy) Benzyl Ester To intermediate 65 (1 equiv.) in DMF (150 mL) was added intermediate 3 (1 equiv.), DMAP (0.1 equiv.) and DIC (1.1 equiv.). The reaction was stirred at rt while it was followed by tlc [CH₂Cl₂/MeOH (98:2); Rf=0.85]. The reaction was evaporated to dryness, the residue treated with NaOH (1N) and extracted with CH₂Cl₂ (5×100 mL). The combined organic layers were dried over Na₂SO₄, filtered and the solvent evaporated to to afford crude example 11. After chromatography eluting with CH₂Cl₂/MeOH (80:20) the title compound was obtained as a clear oil that solidified upon sitting (44%).

Mp 72° C.

EXAMPLE 12

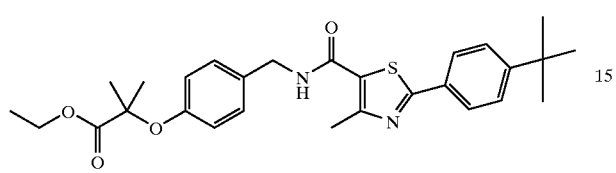

2-Methyl-2-[4-{[(4-methyl-2-[4-tertbutylphenyl]-thiazol-5-ylcarbonyl)amino]methyl}phenoxy] propionic Acid Ethyl Ester Intermediate 24 and Intermediate 68 were reacted as described in general procedure 6 to afford the title compound as a white solid (72%). Chromatographed: CH₂Cl₂, then CH₂Cl₂/MeOH (99:1), then CH₂Cl₂/MeOH (98:2).

MS m/z 495 (M+1).

EXAMPLE 13

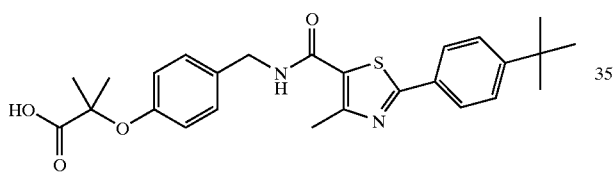

2-Methyl-2-[4-{[(4-methyl-2-[4-tertbutylphenyl]-thiazol-5-ylcarbonyl)amino]methyl}phenoxy] propionic Acid Example 12 was reacted as described in general procedure 8 to afford the title compound as a white solid (22%).

MS m/z 466 (M+1).

EXAMPLE 14

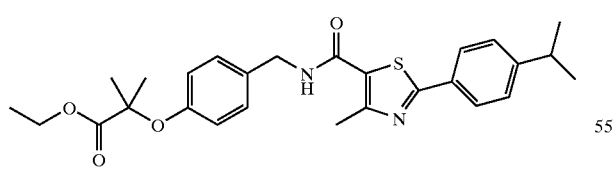

2-Methyl-2-[4-{[(4-methyl-2-[4-isopropylphenyl]-thiazol-5-ylcarbonyl)amino]methyl}phenoxy] propionic Acid Ethyl Ester Intermediate 25 and Intermediate 68 were reacted as described in general procedure 6 to afford the title compound as a white solid (54%). Chromatographed: CH₂Cl₂, then CH₂Cl₂/MeOH (99:1), then CH₂Cl₂/MeOH (98:2).

MS m/z 481 (M+1).

EXAMPLE 15

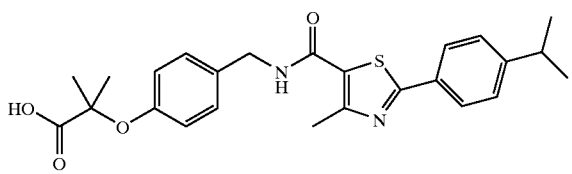

2-Methyl-2-[4-{[(4-methyl-2-[4-isopropylphenyl]-thiazol-5-ylcarbonyl)amino]methyl}phenoxy] propionic Acid Example 14 was reacted as described in general procedure 8 to afford the title compound as a white solid (100%).

MS m/z 453 (M+1).

EXAMPLE 16

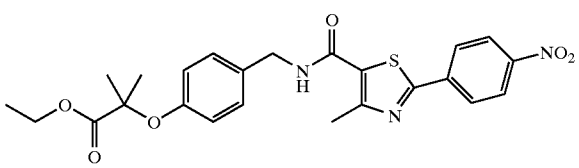

2-Methyl-2-[4-{[(4-methyl-2-[4-nitrophenyl]-thiazol-5-ylcarbonyl)amino]methyl}phenoxy] propionic Acid Ethyl Ester Intermediate 26 and Intermediate 68 were reacted as described in general procedure 7 to afford the title compound as a brownish yellow oil (71%). Chromatographed: CH₂Cl₂/MeOH (99.5:0.5). ¹H NMR (CDCl₃): δ 8.15 (d, 2H), 7.95 (d, 2H), 7.15 (d, 2H), 6.75 (d, 2H), 6.15 (t, 1H), 4.45 (d, 2H), 4.15 (q, 2H), 2.65 (s, 3H), 1.50 (s, 6H), 1.15 (t, 3H).

EXAMPLE 17

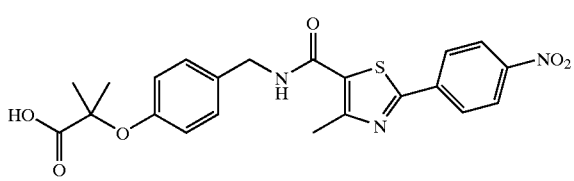

2-Methyl-2-[4-{[(4-methyl-2-[4-nitrophenyl]-thiazol-5-ylcarbonyl)amino]methyl}phenoxy] propionic Acid Example 16 was reacted as described in general procedure 8 to afford the title compound as a yellow solid (34%).

Mp 164° C.

EXAMPLE 18

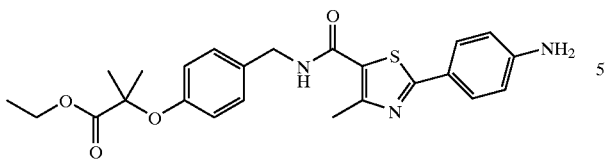

2-Methyl-2-[4-{[(4-methyl-2-[4-aminophenyl]-thiazol-5-ylcarbonyl)amino]methyl}phenoxy] propionic Acid Ethyl Ester To intermediate 16 in EtOH (75 mL) was added 10% Pd/C (0.01 equiv.). The reaction was degassed and place under an atmosphere of $H_2$ at rt for 18 h. The reaction was filtered through celite and the solvent removed under vacuum to afford the title compound as a yellow oil (100%).

MS m/z 454 (M+1).

EXAMPLE 19

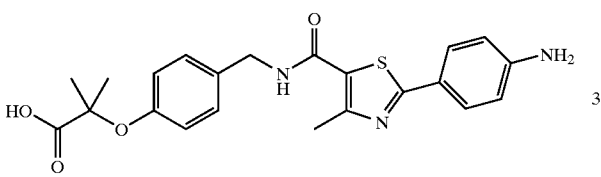

2-Methyl-2-[4-{[(4-methyl-2-[4-aminophenyl]-thiazol-5-ylcarbonyl)amino]methyl}phenoxy] propionic Acid Example 18 was reacted as described in general procedure 8 to afford the title compound as a yellow solid (80%).

MS m/z 426 (M+1).

EXAMPLE 20

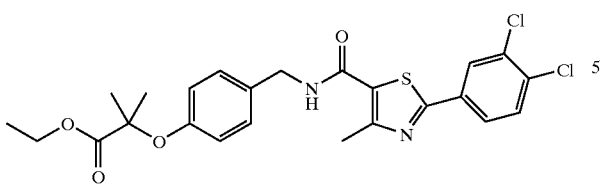

2-Methyl-2-[4-{[(4-methyl-2-[3,4-dichlorophenyl]-thiazol-5-ylcarbonyl)amino]methyl}phenoxy] propionic Acid Ethyl Ester Intermediate 27 and Intermediate 68 were reacted as described in general procedure 7 to afford the title compound as a white solid (55%). Chromatographed: $CH_2Cl_2$, then $CH_2Cl_2$/MeOH (99.5:0.5).

MS m/z 507.

EXAMPLE 21

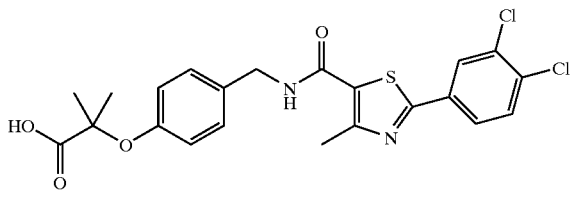

2-Methyl-2-[4-{[(4-methyl-2-[3,4-dichlorophenyl]-thiazol-5-ylcarbonyl)amino]methyl}phenoxy] propionic Acid Example 2 was reacted as described in general procedure 8 to afford the title compound as a white solid (84%).

MS m/z 480 (M+1).

EXAMPLE 22

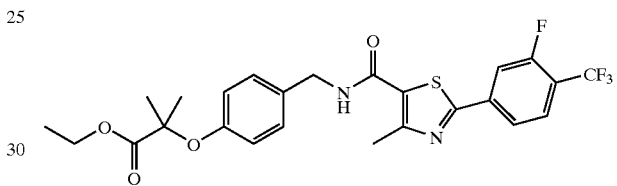

2-Methyl-2-[4-{[(4-methyl-2-[3-fluoro-4-trifluoromethylphenyl]-thiazol-5-ylcarbonyl)amino] methyl}phenoxy]propionic Acid Ethyl Ester Intermediate 28 and Intermediate 68 were reacted as described in general procedure 6 to afford the title compound as a clear oil (52%). Chromatographed: cyclohexane/EtOAc (9:1 to 7:3). $^1$H NMR (DMSO-$d_6$): δ 8.90 (t, 1H), 8.00 (m, 3H), 7.25 (d, 2H), 6.75 (d, 2H), 4.40 (d, 2H), 4.15 (q, 2H), 2.65 (s, 3H), 1.55 (s, 6H), 1.15 (t, 3H).

EXAMPLE 23

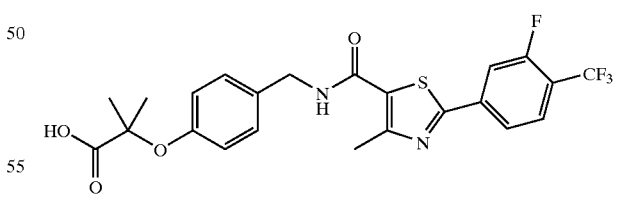

2-Methyl-2-[4-{[(4-methyl-2-[3-fluoro-4-trifluoromethylphenyl]-thiazol-5-ylcarbonyl)amino] methyl}phenoxy]propionic Acid Example 22 was reacted as described in general procedure 8 to afford the title compound as a white solid (70%).

MS (AP−) m/z 495 (M−1).

EXAMPLE 24

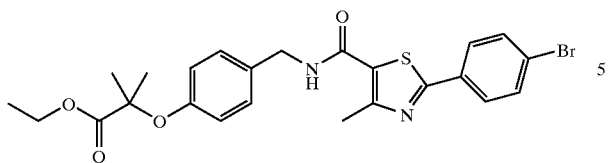

2-Methyl-2-[4-{[(4-methyl-2-[4-bromophenyl]-thiazol-5-ylcarbonyl)amino]methyl}phenoxy] propionic Acid Ethyl Ester Intermediate 29 and Intermediate 68 were reacted as described in general procedure 7 to afford the title compound as a white solid (52%). Chromatographed: $CH_2Cl_2$, then $CH_2Cl_2$/MeOH (99.5:0.5), then $CH_2Cl_2$/MeOH (99:1). $^1$H NMR (CDCl$_3$): δ 7.55 (d, 2H), 7.35 (d, 2H), 7.05 (d, 2H), 6.65 (d, 2H), 6.25 (t, 1H), 4.35 (d, 2H), 4.10 (q, 2H), 2.55 (s, 3H), 1.45 (s, 6H), 1.10 (t, 3H).

EXAMPLE 25

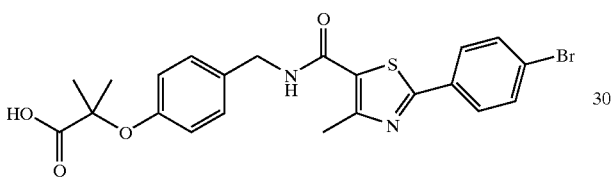

2-Methyl-2-[4-{[(4-methyl-2-[4-bromophenyl]-thiazol-5-ylcarbonyl)amino]methyl}phenoxy] propionic Acid Example 24 was reacted as described in general procedure 8 to afford the title compound as a white solid (90%).

MS m/z 489.

EXAMPLE 26

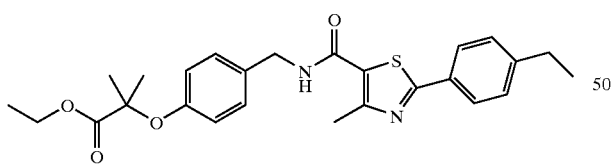

2-Methyl-2-[4-{[(4-methyl-2-[4-ethylphenyl]-thiazol-5-ylcarbonyl)amino]methyl}phenoxy] propionic Acid Ethyl Ester Intermediate 30 and Intermediate 68 were reacted as described in general procedure 6 to afford the title compound as a clear oil (54%). Chromatographed: cyclohexane/EtOAc (8:2 to 6:4). $^1$H NMR (DMSO-d$_6$): δ 8.55 (t, 1H), 7.65 (d, 2H), 7.10 (d, 2H), 7.00 (d, 2H), 6.55 (d, 2H), 4.15 (d, 2H), 3.95 (q, 2H), 2.45 (q, 2H), 2.40 (s, 3H), 1.30 (s, 6H), 1.00 (t, 3H), 0.95 (t, 3H).

EXAMPLE 27

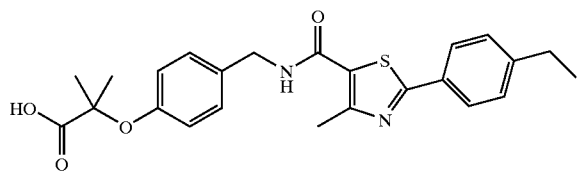

2-Methyl-2-[4-{[(4-methyl-2-[4-ethylphenyl]-thiazol-5-ylcarbonyl)amino]methyl}phenoxy] propionic Acid Example 26 was reacted as described in general procedure 8 to afford the title compound as a white solid (62%).

MS m/z 439 (M+1).

EXAMPLE 28

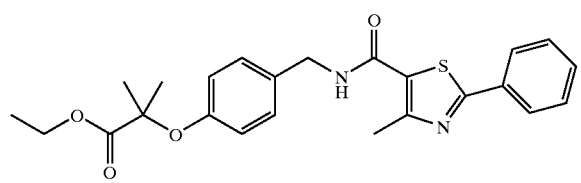

2-Methyl-2-[4-{[(4-methyl-2-phenylthiazol-5-ylcarbonyl)amino]methyl}phenoxy]propionic Acid Ethyl Ester Intermediate 31 and Intermediate 68 were reacted as described in general procedure 7 to afford the title compound as a clear oil (52%). $^1$H NMR (CDCl$_3$): δ 7.85 (m, 2H), 7.35 (m, 3H), 7.15 (d, 2H), 6.75 (d, 2H), 6.00 (t, 1H), 4.50 (d, 2H), 4.15 (q, 2H), 2.65 (s, 3H), 1.5 (s, 6H), 1.2 (t, 3H).

EXAMPLE 29

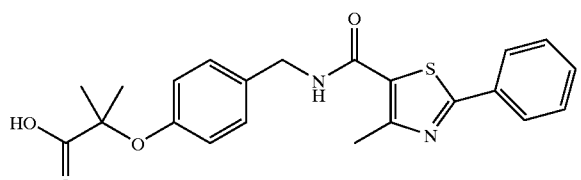

2-Methyl-2-[4-{[(4-methyl-2-phenylthiazol-5-ylcarbonyl)amino]methyl}phenoxy]propionic Acid Example 28 was reacted as described in general procedure 8 to afford the title compound as a white solid (46%).

Mp 179° C.

EXAMPLE 30

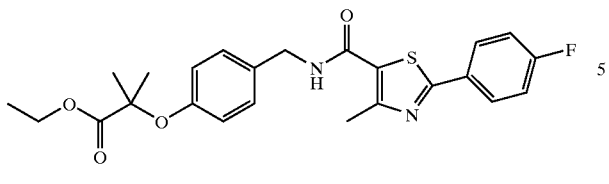

2-Methyl-2-[4-{[(4-methyl-2-[4-fluorophenyl]-thiazol-5-ylcarbonyl)amino]methyl}phenoxy]propionic Acid Ethyl Ester Intermediate 32 and Intermediate 68 were reacted as described in general procedure 7 to afford the title compound as a clear oil that solidified on standing (63%). Chromatographed: $CH_2Cl_2$, then $CH_2Cl_2$/MeOH (99.5:0.5). $^1$H NMR ($CDCl_3$): δ 7.85 (dd, 2H), 7.20 (d, 2H), 7.08 (t, 2H), 6.80 (d, 2H), 6.35 (t, 1H), 4.50 (d, 2H), 4.20 (q, 2H), 2.63 (s, 3H), 1.55 (s, 6H), 1.23 (t, 3H).

EXAMPLE 31

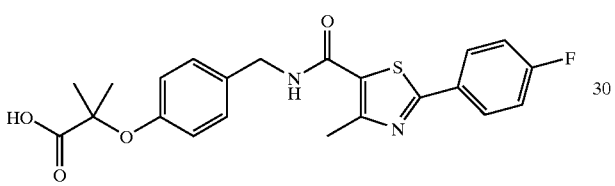

2-Methyl-2-[4-{[(4-methyl-2-[4-fluorophenyl]-thiazol-5-ylcarbonyl)amino]methyl}phenoxy]propionic Acid Example 30 was reacted as described in general procedure 8 to afford the title compound as a white solid (72%).

Mp 159° C.; MS m/z 429 (M+1).

EXAMPLE 32

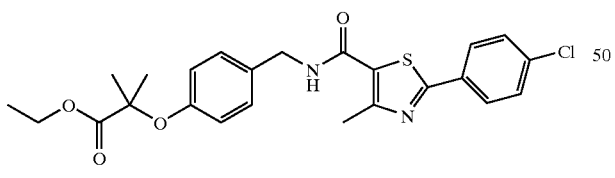

2-Methyl-2-[4-{[(4-methyl-2-[4-chlorophenyl]-thiazol-5-ylcarbonyl)amino]methyl}phenoxy]propionic Acid Ethyl Ester Intermediate 33 and Intermediate 68 were reacted as described in general procedure 7 to afford the title compound as a clear oil (78%). Chromatographed: $CH_2Cl_2$, then $CH_2Cl_2$/MeOH (99:1). $^1$H NMR ($CDCl_3$): δ 7.75 (d, 2H), 7.35 (d, 2H), 7.15 (d, 2H), 6.75 (d, 2H), 6.05 (t, 1H), 4.45 (d, 2H), 4.20 (q, 2H), 2.65 (s, 3H), 1.50 (s, 6H), 1.20 (t, 3H).

EXAMPLE 33

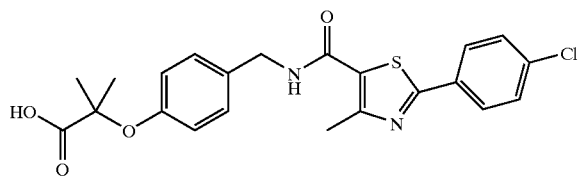

2-Methyl-2-[4-{[(4-methyl-2-[4-chlorophenyl]-thiazol-5-ylcarbonyl)amino]methyl}phenoxy]propionic Acid Example 32 was reacted as described in general procedure 8 to afford the title compound as a white solid (30%).

Mp 131° C.

EXAMPLE 34

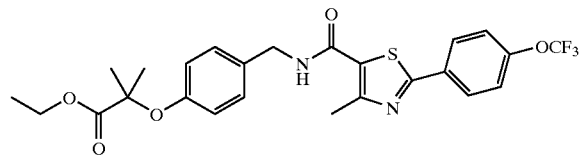

2-Methyl-2-[4-{[(4-methyl-2-[4-trifluoromethoxyphenyl]-thiazol-5-ylcarbonyl)amino]methyl}phenoxy]propionic Acid Ethyl Ester Intermediate 34 and Intermediate 68 were reacted as described in general procedure 6 to afford the title compound as a yellow oil (41%). Chromatographed: $CH_2Cl_2$/MeOH (99.5:0.5). $^1$H NMR ($CDCl_3$): δ 7.90 (d, 2H), 7.20 (d, 2H), 7.15 (d, 2H), 6.75 (d, 2H), 6.05 (t, 1H), 4.45 (d, 2H), 4.15 (q, 2H), 2.65 (s, 3H), 1.50 (s, 6H), 1.20 (t, 3H).

EXAMPLE 35

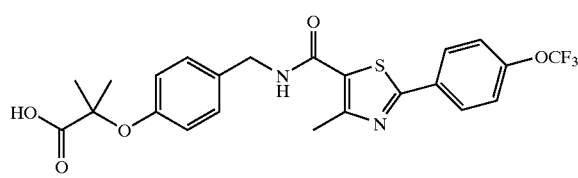

2-Methyl-2-[4-{[(4-methyl-2-[4-trifluoromethoxyphenyl]-thiazol-5-ylcarbonyl)amino]methyl}phenoxy]propionic Acid Example 34 was reacted as described in general procedure 8 to afford the title compound as a brown viscous oil (45%). $^1$H NMR ($CDCl_3$): δ 7.85 (d, 2H), 7.20 (d, 2H), 7.20 (d, 2H), 6.85 (d, 2H), 6.05 (t, 1H), 4.50 (d, 2H), 2.65 (s, 3H), 1.50 (s, 6H).

EXAMPLE 36

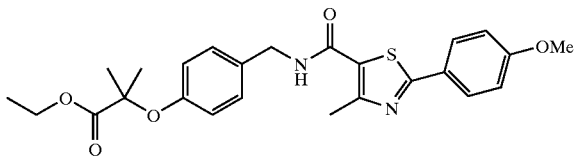

2-Methyl-2-[4-{[(4-methyl-2-[4-methoxyphenyl]-
thiazol-5-ylcarbonyl)amino]methyl}phenoxy]
propionic Acid Ethyl Ester Intermediate 35 and Intermediate 68 were reacted as described in general procedure 6 to afford the title compound as a clear oil that solidified on standing (22%). Chromatographed: cyclohexane/EtOAc (1:1). $^1$H NMR (DMSO-d$_6$): δ 8.75 (t, 1H), 7.90 (d, 2H), 7.20 (d, 2H), 7.05 (d, 2H), 6.75 (d, 2H), 4.35 (d, 2H), 4.15 (q, 2H), 3.80 (s, 3H), 2.55 (s, 3H), 1.50 (s, 6H), 1.15 (t, 3H).

EXAMPLE 37

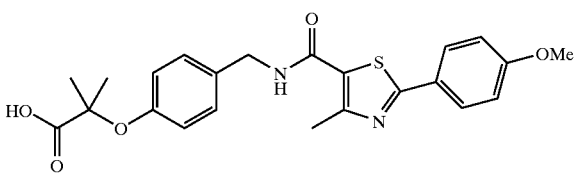

2-Methyl-2-[4-{[(4-methyl-2-[4-methoxyphenyl]-
thiazol-5-ylcarbonyl)amino]methyl}phenoxy]
propionic Acid Example 36 was reacted as described in general procedure 8 to afford the title compound as a beige solid (51%).

MS m/z 441 (M+1).

EXAMPLE 38

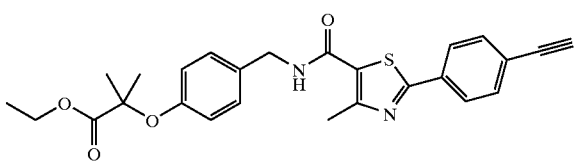

2-Methyl-2-[4-{[(4-methyl-2-[4-acetylenylphenyl]-
thiazol-5-ylcarbonyl)amino]methyl}phenoxy]
propionic Acid Ethyl Ester Intermediate 38 and Intermediate 68 were reacted as described in general procedure 6 to afford the title compound as a brown oil that solidified on standing (84%). Chromatographed: CH$_2$Cl$_2$/EtOAc (95:5).

MS m/z 463 (M+1).

EXAMPLE 39

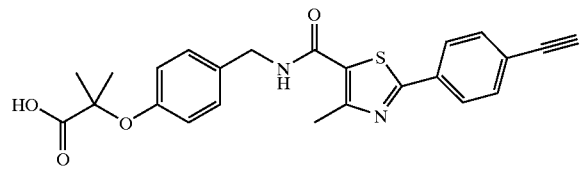

2-Methyl-2-[4-{[(4-methyl-2-[4-acetylenylphenyl]-
thiazol-5-ylcarbonyl)amino]methyl}phenoxy]
propionic Acid Example 38 was reacted as described in general procedure 8 to afford the title compound as a pale rose solid (44%).

MS (AP−) m/z 433 (M−1).

EXAMPLE 40

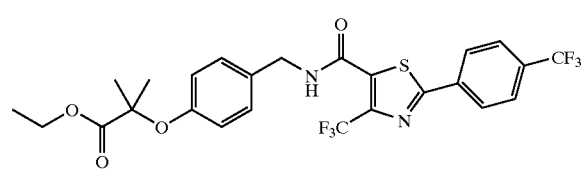

2-Methyl-2-[4-{[(4-trifluoromethyl-2-[4-
trifluoromethylphenyl]-thiazol-5-ylcarbonyl)amino]
methyl}phenoxy]propionic Acid Ethyl Ester Intermediate 42 and Intermediate 68 were reacted as described in general procedure 7 to afford the title compound as a clear oil (69%). Chromatographed: CH$_2$Cl$_2$. $^1$H NMR (CDCl$_3$): δ 8.00 (d, 2H), 7.65 (d, 2H), 7.15 (d, 2H), 6.75 (d, 2H), 6.35 (t, 1H), 4.50 (d, 2H), 4.15 (q, 2H), 1.50 (s, 6H), 1.20 (t, 3H).

EXAMPLE 41

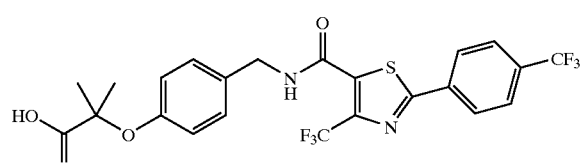

2-Methyl-2-[4-{[(4-trifluoromethyl-2-[4-
trifluoromethylphenyl]-thiazol-5-ylcarbonyl)amino]
methyl}phenoxy]propionic Acid Example 40 was reacted as described in general procedure 8 to afford the title compound as a clear oil that precipitated in pentane as a white solid (19%). Chromatographed: CH$_2$Cl$_2$/MeOH (95:5), then CH$_2$Cl$_2$/MeOH/AcOH (95:5:2 mL). $^1$H NMR (DMSO-d$_6$): δ 9.55 (t, 1H), 8.25 (d, 2H), 8.00 (d, 2H), 7.25 (d, 2H), 6.85 (d, 2H), 4.45 (d, 2H), 1.55 (s, 6H).

EXAMPLE 42

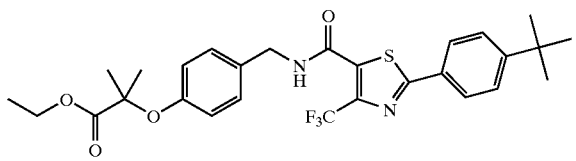

2-Methyl-2-[4-{[(4-trifluoromethyl-2-[4-tertbutylphenyl]-thiazol-5-ylcarbonyl)amino]methyl}phenoxy]propionic Acid Ethyl Ester Intermediate 42 and Intermediate 68 were reacted as described in general procedure 7 to afford the title compound as a clear oil (21%). Chromatographed: $CH_2Cl_2$. $^1H$ NMR ($CDCl_3$): δ 7.85 (d, 2H), 7.45 (d, 2H), 7.25 (d, 2H), 6.85 (d, 2H), 6.40 (t, 1H), 4.60 (d, 2H), 4.25 (q, 2H), 1.60 (s, 6H), 1.35 (s, 9H), 1.25 (t, 3H).

EXAMPLE 43

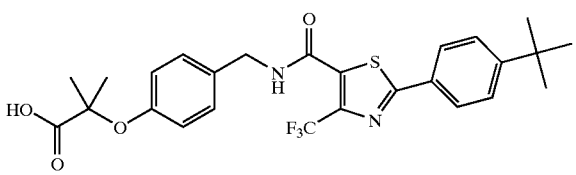

2-Methyl-2-[4-{[(4-trifluoromethyl-2-[4-tertbutylphenyl]-thiazol-5-ylcarbonyl)amino]methyl}phenoxy]propionic Acid Example 42 was reacted as described in general procedure 8 to afford the title compound as a clear oil that precipitated in pentane as a white solid (100%).

MS m/z 521 (M+1).

EXAMPLE 44

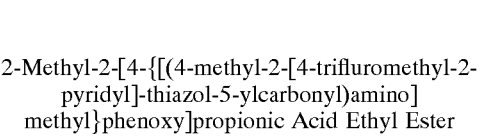

2-Methyl-2-[4-{[(4-methyl-2-[4-trifluromethylphenyl]-oxazol-5-ylcarbonyl)amino]methyl}phenoxy]propionic Acid Ethyl Ester Intermediate 52 and Intermediate 68 were reacted as described in general procedure 7 to afford the title compound as a clear oil (58%). Chromatographed: $CH_2Cl_2$/MeOH (99.5:0.5). $^1H$ NMR ($CDCl_3$): δ 8.05 (d, 2H), 7.65 (d, 2H), 7.25 (t, 1H), 7.15 (d, 2H), 6.75 (d, 2H), 4.50 (d, 2H), 4.15 (q, 2H), 2.70 (s, 3H), 1.50 (s, 6H), 1.20 (t, 3H).

EXAMPLE 45

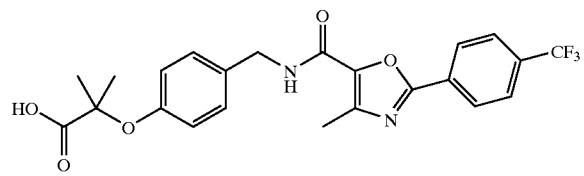

2-Methyl-2-[4-{[(4-methyl-2-[4-trifluoromethylphenyl]-oxazol-5-ylcarbonyl)amino]methyl}phenoxy]propionic Acid Example 44 was reacted as described in general procedure 8 to afford the title compound as a yellow solid (98%).

MS (AP−) m/z 461 (M−1).

EXAMPLE 46

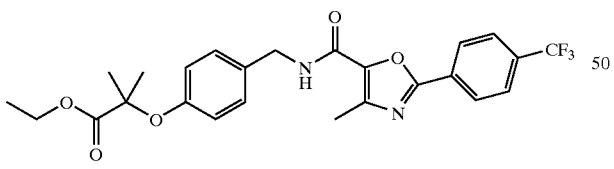

2-Methyl-2-[4-{[(4-methyl-2-[4-trifluromethyl-2-pyridyl]-thiazol-5-ylcarbonyl)amino]methyl}phenoxy]propionic Acid Ethyl Ester Intermediate 54 and Intermediate 68 were reacted as described in general procedure 6 to afford the title compound as a clear oil (58%). Chromatographed: $CH_2Cl_2$/MeOH (99.5:0.5).

MS m/z 508 (M+1).

EXAMPLE 47

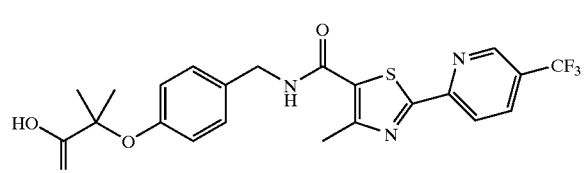

2-Methyl-2-[4-{[(4-methyl-2-[4-trifluoromethyl-2-pyridyl]-thiazol-5-ylcarbonyl)amino]methyl}phenoxy]propionic Acid Example 46 was reacted as described in general procedure 8 to afford the title compound as a white solid (11%; mixture of the free base and hydrochloride salt). $^1H$ NMR ($CDCl_3$): δ 8.75 (s, 1H), 8.20 (d, 2H), 7.95 (d, 2H), 7.15 (d, 2H), 6.85 (d, 2H), 6.20 (t, 1H), 4.45 (d, 2H), 2.65 (s, 3H), 1.50 (s, 6H).

EXAMPLE 48

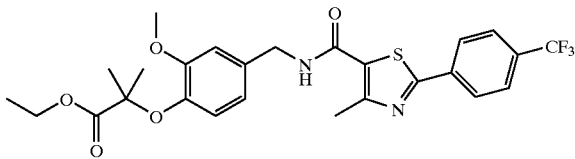

2-Methyl-2-[2-methoxy-4-{[(4-methyl-2-[4-trifluromethylphenyl]-thiazol-5-ylcarbonyl)amino]methyl}phenoxy]propionic Acid Ethyl Ester Intermediate 3 and Intermediate 57 were reacted as described in general procedure 6 to afford the title compound as a clear oil (37%).

MS m/z 537 (M+1).

EXAMPLE 49

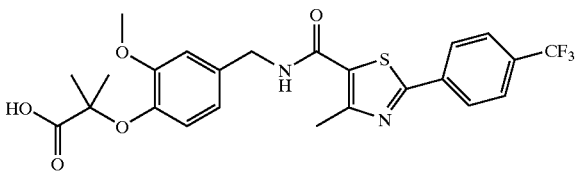

2-Methyl-2-[2-methoxy-4-{[(4-methyl-2-[4-trifluoromethylphenyl]-thiazol-5-ylcarbonyl)amino]methyl}phenoxy]propionic Acid Example 48 was reacted as described in general procedure 8 to afford the title compound as a white solid (53%).

MS m/z 508.

EXAMPLE 50

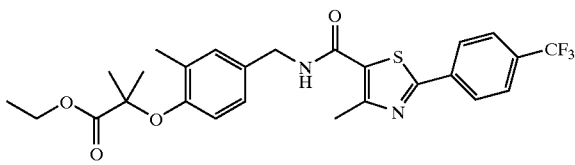

2-Methyl-2-[2-methyl-4-{[(4-methyl-2-[4-trifluromethylphenyl]-thiazol-5-ylcarbonyl)amino]methyl}phenoxy]propionic Acid Ethyl Ester Intermediate 3 and Intermediate 63 were reacted as described in general procedure 6 to afford the title compound as a white solid (33%). $^1$H NMR (CDCl$_3$): δ 7.95 (d, 2H), 7.65 (d, 2H), 7.05 (d, 1H), 6.95 (dd, 1H), 6.55 (d, 1H), 5.95 (t, 1H), 4.45 (d, 2H), 4.15 (q, 2H), 2.65 (s, 3H), 2.15 (s, 3H), 1.50 (s, 6H), 1.15 (t, 3H).

EXAMPLE 51

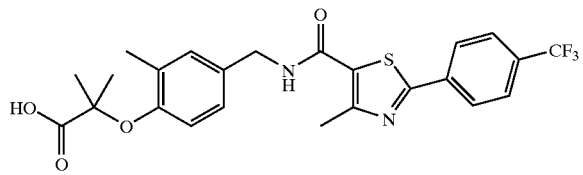

2-Methyl-2-[2-methyl-4-{[(4-methyl-2-[4-trifluoromethylphenyl]-thiazol-5-ylcarbonyl)amino]methyl}phenoxy]propionic Acid Example 50 was reacted as described in general procedure 8 to afford the title compound as a white solid (93%).
MS m/z 493 (M+1).

EXAMPLE 52

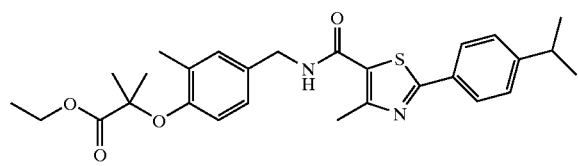

2-Methyl-2-[2-methyl-4-{[(4-methyl-2-[4-isopropylphenyl]-thiazol-5-ylcarbonyl)amino]methyl}phenoxy]propionic Acid Ethyl Ester Intermediate 25 and Intermediate 63 were reacted as described in general procedure 6 to afford the title compound as a white solid (51%).
Mp 129–131° C.

EXAMPLE 53

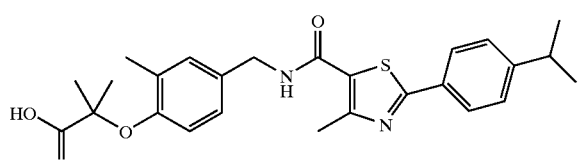

2-Methyl-2-[2-methyl-4-{[(4-methyl-2-[4-isopropylphenyl]-thiazol-5-ylcarbonyl)amino]methyl}phenoxy]propionic Acid Example 62 was reacted as described in general procedure 8 to afford the title compound as a white solid (85%).
MS m/z 467 (M+1).

EXAMPLE 54

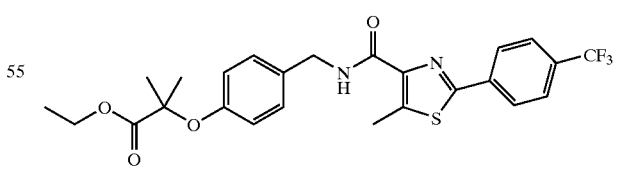

2-Methyl-2-[4-{[(5-methyl-2-[4-trifluoromethylphenyl]-thiazol-4-ylcarbonyl)amino]methyl}phenoxy]propionic Acid Ethyl Ester Intermediate 44 and Intermediate 68 were reacted as described in general procedure 6 to afford the title compound as a white solid (85%).
MS m/z 507 (M+1).

EXAMPLE 55

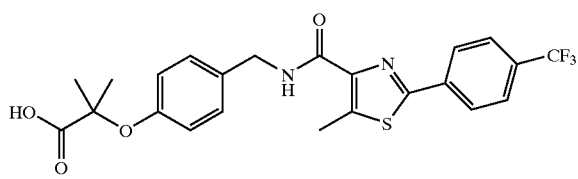

2-Methyl-2-[4-{[(5-methyl-2-[4-trifluoromethylphenyl]-thiazol-4-ylcarbonyl)amino]methyl}phenoxy]propionic Acid Example 54 was reacted as described in general procedure 8 to afford the title compound as a white solid (39%).
MS m/z 479 (M+1).

EXAMPLE 56

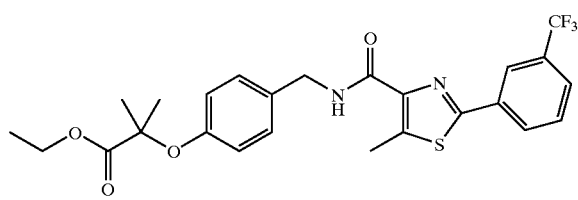

2-Methyl-2-[4-{[(5-methyl-2-[3-trifluoromethylphenyl]-thiazol-4-ylcarbonyl)amino]methyl}phenoxy]propionic Acid Ethyl Ester Intermediate 25 and Intermediate 63 were reacted as described in general procedure 6 to afford the title compound as a pale yellow oil (43%).
MS m/z 507 (M+1).

EXAMPLE 57

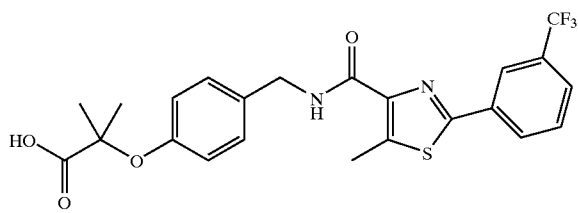

2-Methyl-2-[4-{[(5-methyl-2-[3-trifluoromethylphenyl]-thiazol-4-ylcarbonyl)amino]methyl}phenoxy]propionic Acid Example 56 was reacted as described in general procedure 8 to afford the title compound as a white solid (74%).
MS m/z 479 (M+1).

The following Intermediates and ligands were prepared for the binding and transfection assays described below.

(i) 2-(4-(2-(2,3-Ditritio-1-heptyl-3-(2,4-difluorophenyl)ureido)ethyl)phenoxy)-2-methylbutanoic Acid This compound was used as a control radioligand for hPPARα in the binding assay described below. It is also described in WO00/08002, the synthesis is reproduced below;

Intermediate A: 2-(4-(2-(Phenylmethyloxycarbonylamino)ethyl)phenoxy)-2-methylbutanoic Acid A solution of 4-(2-(phenylmethyloxycarbonylamino)ethyl)phenol (5.74 g; 21.16 mmole) in 2-butanone (17 mL) and chloroform (6 g) was added dropwise to a mixture of sodium hydroxide (9.0 g; 225 mmole) and 2-butanone (67 mL) whilst keeping the reaction temperature below 30° C. The mixture was allowed to stir at 30° C. for 4 h. Ether (100 mL) was added and the resultant solid was collected by filtration and washed with ether (100 mL). The solid was dissolved in water (70 mL) and any residual ether removed by evaporation. 1N Hydrochloric acid was added to adjust the pH to 1, and the resulting oil was extracted with dichloromethane (3×50 mL). The combined extracts were dried ($Na_2SO_4$) and evporated to afford a yellow oil (3.82 g; 49%). $^1$H-NMR ($CDCl_3$) δ 7.26 (s, 5H), 7.09 (d, 2H, J=7.9 Hz), 6.88 (d, 2H, J=8.4 Hz), 5.09 (s, 2H), 4.75 (br s, 1H), 3.42–3.44 (m, 2H), 2.75 (t, 2H, J=6.7 Hz), 1.92–2.00 (m, 2H), 1.47 (s, 3H), 1.04 (t, 3H, J=2.6 Hz). Mass spectrometry $ES^+$, m/e $(M+H)^+$=372.

Intermediate B: Methyl 2-(4-(2-(Phenylmethyloxycarbonylamino)ethyl)phenoxy)-2-methyl Butyrate A solution of Intermediate A (2.0 g; 5.38 mmole) in dimethylformamide (12 mL) was treated with potassium carbonate (2.23 g; 16.14 mmole) and methyl iodide (1.54 g; 10.76 mmole) and the resulting mixture stirred at 23° C. for 2 h. The mixture was filtered and the solid collected was washed with ethyl acetate (70 mL). The filtrate was washed with brine (4×50 mL), dried ($Na_2SO_4$) and evaporated. The residue was purified by chromatography on silica gel using hexane then 33% ethyl acetate-hexane as eluent to afford a colorless oil (1.27 g; 61%).

$^1$H-NMR (DMSO-$d_6$) δ 7.31 (m, 5H), 7.06 (d, 2H, J=8.4 Hz), 6.68 (d, 2H, J=8.4 Hz), 4.98 (s, 2H), 3.67 (s, 3H), 3.15 (m, 2H), 2.62 (t, 2H, J=7.1 Hz), (m, 2H), 1.38 (s, 3H), 0.86 (t, 3H, J=7.3 Hz). Mass spectrometry $ES^+$, m/e $(M+Na)^+$=408.

Intermediate C: Methyl 2-(4-(2-Aminoethyl)phenoxy)-2-methyl Butyrate Acetate Salt A solution of Intermediate B (1.27 g; 3.29 mmole) in methanol (50 mL) and acetic acid (0.4 g) was treated with 10% palladium on carbon and shaken in a hydrogen atmosphere (50 psi) for 2 h. The catalyst was filtered through celite and the solvent was evaporated to afford a yellow oil in quantitative yield (1.04 g).

$^1$H-NMR ($CDCl_3$): δ 7.06 (d, 2H, J=8.4 Hz), 6.77 (d, 2H, J=8.4 Hz), 6.70 (br s, 2H), 3.76 (s, 3H), 3.02 (br s, 2H), 2.82 (m, 2H), 1.99 (s, 3H), 1.92 (m, 2H), 1.48 (s, 3H), 0.96 (t, 3H, J=7.4 Hz). Mass spectrometry $ES^+$, m/e $(M+H)^+$=252.

Intermediate D: Methyl 2-(4-(2-(2,4-Dinitrophenylsulfonylamino)ethyl)phenoxy)-2-methyl Butyrate A solution of Intermediate C (2 g; 6.42 mmole) in $CH_2Cl_2$ (40 mL) was treated with saturated sodium bicarbonate solution and the organic layer was separated. The aqueous layer was extracted with $CH_2Cl_2$ (5×50 mL) and the combined organic layers were dried ($Na_2SO_4$) and evaporated to afford the free base as a yellow oil (1.61 g; 100%). This was dissolved in $CH_2Cl_2$ (40 mL) and treated with pyridine (0.45 g; 5.61 mmole) and 2,4-dinitrophenylsulfonyl chloride (1.5 g; 5.61 mmole), and the mixture was allowed to stir at 23° C. for 3 h. Water (60 mL) was added and the organic layer separated, washed with water (3×40 mL) and saturated sodium bicarbonate (40 mL). The organic layer was dried (Na$_2$SO$_4$) and evaporated and the residue purified by chromatography using 15–20% EtOAc-Hexane as eluent to afford a light yellow solid (1.38 g; 51%). $^1$H-NMR (CDCl$_3$): δ 8.63 (d, 1H, J=2.3 Hz), 8.49 (dd, 1H, J=8.4 Hz, J'=2.3 Hz), 8.07 (d, 1H, J=8.4 Hz), 6.89 (d, 2H, J=8.4 Hz), 6.54 (d, 2H, J=8.4 Hz), 5.34 (t, 1H, J=5.3 Hz), 3.78 (s, 3H), 3.48 (q, 2H, J=8.3 Hz), 2.75 (t, 2H, J=6.6 Hz), 1.92 (m, 2H), 1.42 (s, 3H), 0.93 (t, 3H, J=7.5 Hz).

Intermediate E: Methyl 2-(4-(2-((2,4-Dinitrophenylsulfonyl)(hept-2-en-1-yl))amino)ethyl)phenoxy)-2-methyl Butyrate A solution of Intermediate D (315 mg; 0.654 mmole) in THF (15 mL) was treated with triphenylphosphine (343 mg; 1.308 mmole), hept-2-en-1-ol (150 mg; 1.308 mmole) and diethylazodicarboxylate (228 mg; 1.308 mmole) and the mixture allowed to stir at 23° C. for 1 h. The solvent was evaporated and the residue purified by chromatography using 10–15% EtOAc-Hexane as eluent to afford a semi-solid (400 mg; >100%). TLC and NMR shows that the desired compound is present along with 1,2-(diethoxycarbonyl)hydrazine.

Intermediate F: Methyl 2-(4-(2-(Hept-2-en-1-ylamino)ethyl)phenoxy)-2-methyl Butanoate A solution of Intermediate E (400 mg; 0.654 mmole) in CH$_2$Cl$_2$ (5 mL) was treated with triethylamine (132 mg; 1.308 mmole) and mercaptoacetic acid (78 mg; 0.85 mmole) and the mixture was allowed to stir at 23° C. for 1 h. The mixture was diluted with EtOAc (30 mL) and washed with water (3×20 mL) and aqueous sodium bicarbonate (30 mL). The organic layer was dried (Na$_2$SO$_4$), evaporated and the residue purified by chromatography using 10% EtOAc-Hexane then 50% EtOAc-Hexane then MeOH as eluent to afford an oil (177 mg; 78% from intermediate 24).

$^1$H-NMR (CDCl$_3$): δ 7.06 (d, 2H, J=7.5 Hz), 6.75 (d, 2H, J=7.5 Hz), 5.59 (m, 2H), 3.76 (s, 3H), 3.30 (d, 2H, J=6.3 Hz), 2.87 (m, 4H), 1.96 (m, 4H), 1.47 (s, 3H), 1.28 (m, 5H), 0.96 (t, 3H, J=7.6 Hz), 0.86 (t, 3H, J=6.9 Hz).

Intermediate G: Methyl 2-(4-(2-(1-Hept-2-enyl-3-(2,4-difluorophenyl)ureido)ethyl)phenoxy)-2-methylbutyrate A solution of Intermediate F (157 mg; 0.452 mmole) in methylene chloride (5 mL) was treated with 2,4-difluorophenylisocyanate (140 mg; 0.904 mmole) and the mixture allowed to stand at 23° C. for 18 h. The solvent was evaporated and the residue purified by chromatography on silica gel using 10% then 15% ethyl acetate-hexane as eluent to afford a yellow semi-solid (212 mg; 93%). Contaminated with bis-(2,4-difluorophenyl)urea which co-elutes on column.

$^1$H-NMR (CDCl$_3$): δ 8.85 (br s, 1H), 8.02 (m, 1H), 7.09 (d, 2H, J=8.4 Hz), 6.77–6.90 (m, 4H), 5.70 (m, 1H), 5.36 (m, 1H), 3.76 (s, 3H), 3.54 (t, 2H, J=7.3 Hz), 2.84 (t, 2H, J=7.1 Hz), 1.55 (br s, 1H), 1.46 (s, 3H), 1.25–1.35 (m, 5H), 0.96 (t, 3H, J=7.3 Hz), 0.88 (t, 3H, J=7.4 Hz). Mass spectrometry CI/AP$^+$, m/e (M+H)$^+$=503.

2-(4-(2-(1-Hept-2-enyl-3-(2,4-difluorophenyl)ureido)ethyl)phenoxy)-2-methylbutanoic Acid (Radioligand Precursor)

A solution of Intermediate G (370 mg; 0.736 mmole) in methanol (15 mL) was treated with 1N NaOH (7.5 mL) and the mixture heated under reflux for 2 h. The mixture was acidified with 1N HCl and extracted with ethyl acetate (3×25 mL). The combined organic layers were washed with brine, dried (Na$_2$SO$_4$) and evaporated. The residue was purified by chromatography on silica gel using 20% ethyl acetate-hexane then ethyl acetate as eluent to afford a tan oil (280 mg; 78%).

$^1$H-NMR (CDCl$_3$) δ 7.95–8.09 (m, 1H), 7.14 (d, 2H, J=7.1 Hz), 6.90 (d, 2H, J=7.4 Hz), 6.81 (d, 2H, J=5.2 Hz), 5.66 (m, 1H), 5.37 (m, 1H), 3.56 (t, 2H, J=7.4 Hz), 2.87 (t, 2H, J=7.4 Hz), 2.00 (m, 4H), 1.44 (s, 3H), 1.27 (m, 6H), 1.03 (t, 3H, J=7.3 Hz), 0.88 (t, 3H, J=7.3 Hz). Mass spectrometry ES$^-$, m/e (M+H)$^+$=489.

Radioligand: 2-(4-(2-(2,3-Ditritio-1-heptyl-3-(2,4-difluorophenyl)ureido)ethyl)phenoxy)-2-methylbutanoic Acid A solution of radioligand precursor prepared above (10 mg) in anhydrous DMF (3.5 mL) was transferred to a reaction vessel containing 10% Pd/C (9.8 mg). The reaction vessel was evacuated and degassed via one freeze-thaw-evacuation cycle and then exposed to tritium gas (10.1 Ci). After 4 h, the mixture was filtered through celite, evaporated and the residue dissolved in acetonitrile. A portion of this solution (0.8 mL, 26.6 mCi) was purified by HPLC (Dynamax C8, 25 min gradient from 4:1 acetonitrile:0.1% TFA to 9:1 acetonitrile: 0.1% TFA, 235 nm). Fractions containing pure material were combined and evaporated under nitrogen. The residue was redissolved in acetonitrile to provide a solution of the title compound (82.0 Ci/mmol, radiochemical purity, 99%).

2-(4-(2-(1-Heptyl-3-(2,4-difluorophenyl)ureido)ethyl)phenoxy)-2-methylbutanoic Acid The unlabelled ("cold") version of the above radioligand was prepared as a control. A solution of Intermediate G (10 mg) in anhydrous DMF (3.5 mL) was transferred to a reaction vessel containing 10% Pd/C (9.8 mg). The reaction vessel was evacuated and degassed via one freeze-thaw-evacuation cycle and then exposed to hydrogen gas. After 4 h, the mixture was filtered through celite and evaporated. The residue was purified by chromatography using 2% MeOH/CH$_2$Cl$_2$ as eluent to afford a gum (7 mg).

(ii) 2-{2-Methyl-4-[({4-methyl-2-[4-(trifluoromethyl)phenyl]-1,3-thiazol-5-yl}methyl)sulfanyl]phenoxy}acetic Acid This compound was used as a positive control for PPAR delta in the transfaction assay and may be prepared as demonstrated below:

Intermediate H

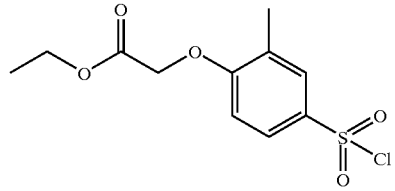

Chlorosulfonic acid (15 mL) was cooled to 0° C. then 10.0 g (0.05M) of ethyl (2-methylphenoxyacetate was added over 10 m. The reaction mixture was stirred at 0–5° C. for 30 m, the bath was removed and stirring continued for 2 h. The reaction mixture was poured into ice, forming a white solid which was washed with ice water and dried under high vacuum affording the title compound (12.846 g, 86%).

2-{2-Methyl-4-[({4-methyl-2-[4-(trifluoromethyl) phenyl]-1,3-thiazol-5-yl}methyl)sulfanyl] phenoxy}acetic Acid

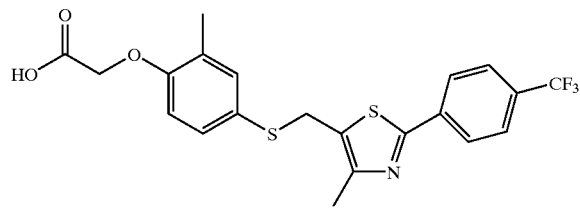

Intermediate H (4.68 g, 16 mM) was refluxed with 9.6 g of tin powder in ethanol (20 mL) and dioxane/HCl (20 mL). After 3 h the reaction mixture was poured into ice and CH$_2$Cl$_2$ (200 mL) and filtered. The phases were separated and the aqueous layer was extracted 2×50 mL CH$_2$Cl$_2$. The combined organic layers were dried (MgSO$_4$), filtered and evaporated to yield 3.5 g (97%). This material readily forms disulfides and therefore was used immediately. It was dissolved in acetonitrile (50 mL) with intermediate 2 (4.0 g, 14.0 mM) and Cs$_2$CO$_3$ (10.1 g, 31.0 mM) and stirred for 1 h then diluted with ether (200 mL) and water (200 mL). The phases were separated and the organic phase was washed 2×NaOH 0.1N (50 mL), dried (MgSO$_4$), filtered and evaporated to afford crude product (6.57 g,) which was slurried in hexane:ether (1:1) and filtered to yield pure intermediate 59 (5.0 g, 74%). This material is then be hydrolyzed as described below to prepare the title compound. A solution of the corresponding ester (1 mmol) in THF (10 mL) (in some cases few drops of MeOH were added to help solubility), was treated with 1N LiOH in water (2 mL, 2 mmol), and stirred 16 h at room temperature (when reactions were slow, the temperature was elevated to 50° C.). The solution was neutralized with 1N HCl (2 mL, 2 mmol) and the organic solvent evaporated to afford an aqueous solution with an insoluble product. If the insoluble was a solid, it was filtered and dried to afford the final product. If the insoluble was an oil, it was extracted with EtOAc (30 mL). The organic solution was separated, washed with water (2×30 mL), dried, filtered, and evaporated to afford the final product.

(iii) 2-(2-Methyl-3-[3-{3-(4-cyclohexylamino)-[6-(4-fluorophenylpiperazin-1-yl)][1,3,5]triazin-2-ylamino}propyl]phenylthio)-2-methylpropionic Acid This compound was used as a PPARalpha reference in the transfection assays described below and as prepared according to the following method:

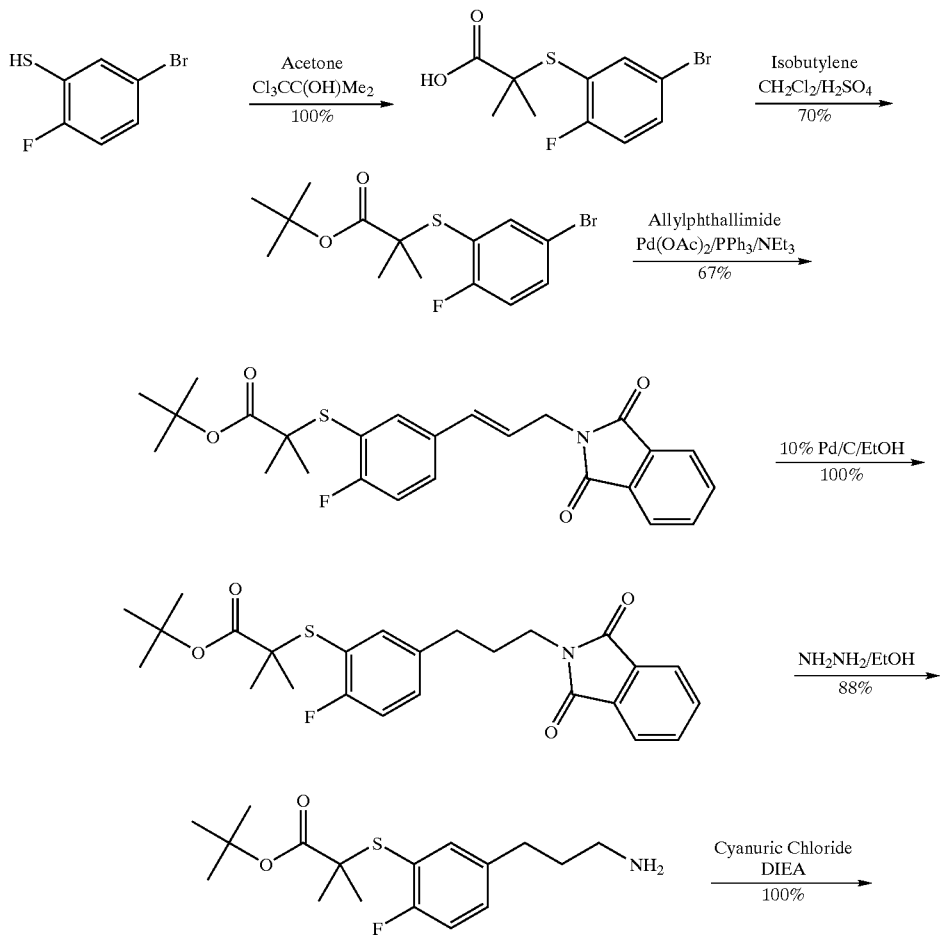

-continued

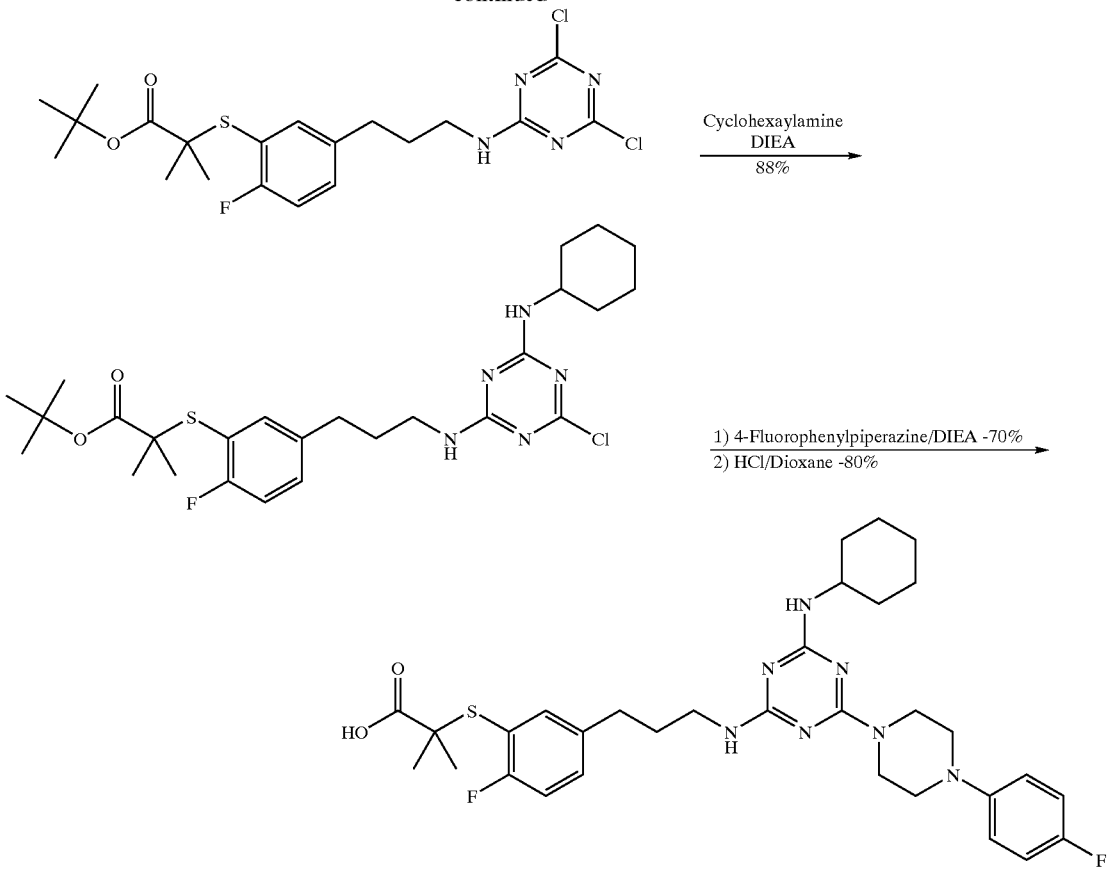

Binding Assay:

Compounds were tested for their ability to bind to hPPAR gamma hPPAR alpha, or PPAR delta using a Scintillation Proximity Assay (SPA). The PPAR ligand binding domain (LBD) was expressed in E. coli as polyHis tagged fusion proteins and purified. The LBD was then labeled with biotin and immobilized on streptavidin-modified scintillation proximity beads. The beads were then incubated with a constant amount of the appropriate radioligand ($^3$H-BRL 49653 for PPAR gamma, radiolabelled 2-(4-(2-(2,3-Ditritio-1-heptyl-3-(2,4-difluorophenyl)ureido)ethyl)phenoxy)-2-methylbutanoic acid for hPPAR alpha and labelled GW 2433 for PPAR delta (see Brown, P. J et al. Chem. Biol. 1997, 4, 909–918. For the structure and synthesis of this ligand)) and variable concentrations of test compound, and after equilibration the radioactivity bound to the beads was measured by a scintillation counter. The amount of nonspecific binding, as assessed by control wells containing 50 μM of the corresponding unlabeled ligand, was subtracted from each data point. For each compound tested, plots of ligand concentration vs. CPM of radioligand bound were constructed and apparent $K_I$ values were estimated from non-linear least squares fit of the data assuming simple competitive binding. The details of this assay have been reported elsewhere (see, Blanchard, S. G. et. al. Development of a Scintillation Proximity Assay for Peroxisome Proliferator-Activated Receptor gamma Ligand Binding Domain. Anal. Biochem. 1998, 257, 112–119).

Transfection Assay:

Compounds were screened for functional potency in transient transfection assays in CV-1 cells for their ability to activate the PPAR subtypes (transactivation assay). A previously established chimeric receptor system was utilized to allow comparison of the relative transcriptional activity of the receptor subtypes on the same target gene and to prevent endogenous receptor activation from complicating the interpretation of results. See, for example, Lehmann, J. M.; Moore, L. B.; Smith-Oliver, T. A.; Wilkison, W. O.; Willson, T. M.; Kliewer, S. A., An antidiabetic thiazolidinedione is a high affinity ligand for peroxisome proliferator-activated receptor γ (PPARγ), J. Biol. Chem., 1995, 270, 12953–6. The ligand binding domains for murine and human PPAR alpha, PPAR gamma, and PPAR delta were each fused to the yeast transcription factor GAL4 DNA binding domain. CV-1 cells were transiently transfected with expression vectors for the respective PPAR chimera along with a reporter construct containing five copies of the GAL4 DNA binding site driving expression of secreted placental alkaline phosphatase (SPAP) and β-galactosidase. After 16 h, the medium was exchanged to DME medium supplemented with 10% delipidated fetal calf serum and the test compound at the appropriate concentration. After an additional 24 h, cell extracts were prepared and assayed for alkaline phosphatase and β-galactosidase activity. Alkaline phosphatase activity was corrected for transfection efficiency using the β-galactosidase activity as an internal standard (see, for example, Kliewer, S. A., et. al. Cell 83, 813–819 (1995)). Rosiglitazone (BRL 49653) was used as a positive control in the hPPAR gamma assay. The positive control in the hPPAR alpha assays was 2-(2-methyl-3-[3-{3-(4-cyclohexylamino)-[6-(4-fluorophenylpiperazin-1-yl)][1,3,5]triazin-2-ylamino}propyl]phenylthio)-2-methylpropionic acid. The positive control for PPAR delta assays was 2-{2-methyl-4-[({4-methyl-2-{trifluoromethyl)phenyl]-1,3-thiazol-5-yl}methyl)sulfanyl]phenoxy}acetic acid.

TABLE 2

PPAR Transactivation activity for selected compounds.

| Example no. | human $_\alpha$EC$_{50}$ µM | human $_\delta$EC$_{50}$ µM | human $_\gamma$EC$_{50}$ µM |
|---|---|---|---|
| Example 1 | 0.017 | 10.000 | 10.000 |
| Example 2 | 0.006 | 2.950 | 10.000 |
| Example 6 | 0.230 | 10.000 | 10.000 |
| Example 10 | 0.108 | 10.000 | 10.000 |
| Example 13 | 0.005 | 10.000 | 0.850 |
| Example 15 | 0.001 | 4.370 | 2.640 |
| Example 17 | 0.027 | 10.000 | 10.000 |
| Example 21 | 0.028 | 10.000 | 10.000 |
| Example 23 | 0.007 | 9.190 | 10.000 |
| Example 25 | 0.010 | 2.700 | 10.000 |
| Example 27 | 0.002 | 4.080 | 8.820 |
| Example 29 | 0.122 | 10.000 | 10.000 |
| Example 31 | 0.044 | 10.000 | 10.000 |
| Example 33 | 0.014 | 5.350 | 10.000 |
| Example 35 | 0.004 | 4.590 | 10.000 |
| Example 37 | 0.020 | 10.000 | 10.000 |
| Example 39 | 0.036 | 2.480 | 10.000 |
| Example 41 | 0.005 | 10.000 | 0.832 |
| Example 45 | 0.400 | 1.640 | 10.000 |
| Example 47 | 0.020 | 7.300 | 10.000 |
| Example 49 | 0.010 | 1.000 | 10.000 |

What is claimed is:

1. A compound of formula (I) and pharmaceutically acceptable salts, solvates and hydrolysable esters thereof

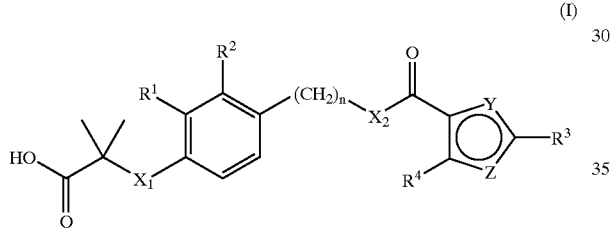

(I)

wherein;

$X_1$ represents O or S;

$R^1$ and $R^2$ independently represent H, halogen, —CH$_3$, or —OCH$_3$;

n represents 1 or 2;

$X_2$ represents NH, NCH$_3$ or O;

One of Y and Z is N, and the other is O or S;

$R^3$ represents phenyl or pyridyl (wherein the N is in position 2 or 3) and is optionally substituted by one or more halogen, NO$_2$, NH$_2$, CF$_3$, OCF$_3$, OC$_{1-6}$ straight or branched alkyl, C$_{1-6}$ straight or branched alkyl, alkenyl or alkynyl with the provision that when $R^3$ is pyridyl, the N is unsubstituted;

$R^4$ represents CF$_3$ or CH$_3$.

2. A compound of claim 1 which is a hPPAR alpha agonist.

3. A compound according to claim 2 which is a selective hPPAR alpha agonist.

4. A compound according to claim 1 wherein $X_1$ represents O.

5. A compound according to claim 1 wherein one of $R^1$ and $R^2$ is H.

6. A compound according to claim 5 wherein $R^1$ and $R^2$ both represent H.

7. A compound according to claim 1 wherein n represents 1.

8. A compound according to claim 1 wherein $X_2$ represents NH.

9. A compound according to claim 1 wherein Z represents N.

10. A compound according to claim 1 wherein Y represents S.

11. A compound according to claim 1 wherein $R^3$ is monosubstituted.

12. A compound according to claim 11 where $R^3$ is monosubstituted with CF$_3$.

13. A compound according to claim 11 wherein $R^3$ is monosubstituted in the para position.

14. A compound according to claim 1 wherein $R^3$ is phenyl.

15. A compound according to claim 1 wherein $R^4$ is CH$_3$.

16. A compound selected from:

2-methyl-2-[4-{[(4-methyl-2-[4-trifluoromethylphenyl]-thiazol-5-ylcarbonyl)amino]ethyl}phenoxy]propionic acid ethyl ester;

N-methyl-2-methyl-2-[4-{[(4-methyl-2-[4-trifluoromethylphenyl]-thiazol-5-ylcarbonyl)amino]ethyl}phenoxy]propionic acid ethyl ester;

4-methyl-2-[4-trifluoromethylphenyl]-thiazol-5-carboxylic acid 4-(1-tertbutyloxycarbonyl-1-methylethoxy) benzyl ester;

2-methyl-2-[4-{[(4-methyl-2-[4-tertbutylphenyl]-thiazol-5-ylcarbonyl)amino]methyl}phenoxy]propionic acid ethyl ester;

2-methyl-2-[4-{[(4-methyl-2-[4-isopropylphenyl]-thiazol-5-ylcarbonyl)amino]methyl}phenoxy] propionic acid ethyl ester;

2-methyl-2-[4-{[(4-methyl-2-[4-nitrophenyl]-thiazol-5-ylcarbonyl)amino]methyl}phenoxy]propionic acid ethyl ester;

2-methyl-2-[4-{[(4-methyl-2-[4-aminophenyl]-thiazol-5-ylcarbonyl)amino]methyl}phenoxy]propionic acid ethyl ester;

2-methyl-2-[4-{[(4-methyl-2-[4-aminophenyl]-thiazol-5-ylcarbonyl)amino]methyl}phenoxy]propionic acid;

2-methyl-2-[4-{[(4-methyl-2-[3,4-dichlorophenyl]-thiazol-5-ylcarbonyl)amino]methyl}phenoxy] propionic acid ethyl ester;

2-methyl-2-[4-{[(4-methyl-2-[3-fluoro-4-trifluoromethylphenyl]-thiazol-5-ylcarbonyl)amino]methyl}phenoxy]propionic acid ethyl ester;

2-methyl-2-[4-{[(4-methyl-2-[4-bromophenyl]-thiazol-5-ylcarbonyl)amino]methyl}phenoxy]propionic acid ethyl ester;

2-methyl-2-[4-{[(4-methyl-2-[4-ethylphenyl]-thiazol-5-ylcarbonyl)amino]methyl}phenoxy]propionic acid ethyl ester;

2-methyl-2-[4-{[(4-methyl-2-phenylthiazol-5-ylcarbonyl)amino]methyl}phenoxy]propionic acid ethyl ester;

2-methyl-2-[4-{[(4-methyl-2-[4-fluorophenyl]-thiazol-5-ylcarbonyl)amino]methyl}phenoxy]propionic acid ethyl ester;

2-methyl-2-[4-{[(4-methyl-2-[4-chlorophenyl]-thiazol-5-ylcarbonyl)amino]methyl}phenoxy]propionic acid ethyl ester;

2-methyl-2-[4-{[(4-methyl-2-[4-trifluoromethoxyphenyl]-thiazol-5-ylcarbonyl)amino]methyl}phenoxy]propionic acid ethyl ester;

2-methyl-2-[4-{[(4-methyl-2-[4-methoxyphenyl]-thiazol-5-ylcarbonyl)amino]methyl}phenoxy]propionic acid ethyl ester;

2-methyl-2-[4-{[(4-methyl-2-[4-acetylenylphenyl]-thiazol-5-ylcarbonyl)amino]methyl}phenoxy]propionic acid ethyl ester;

2-methyl-2-[4-{[(4-trifluoromethyl-2-[4-trifluoromethylphenyl]-thiazol-5-ylcarbonyl)amino]methyl}phenoxy]propionic acid ethyl ester;

2-methyl-2-[4-{[(4-trifluoromethyl-2-[4-tertbutylphenyl]-thiazol-5-ylcarbonyl)amino]methyl}phenoxy]propionic acid ethyl ester;

2-methyl-2-[4-{[(4-trifluoromethyl-2-[4-tertbutylphenyl]-thiazol-5-ylcarbonyl)amino]methyl}phenoxy]propionic acid;

2-methyl-2-[4-{[(4-methyl-2-[4-trifluromethylphenyl]-oxazol-5-ylcarbonyl)amino]methyl}phenoxy]propionic acid ethyl ester;

2-methyl-2-[4-{[(4-methyl-2-[4-trifluromethyl-2-pyridyl]-thiazol-5-ylcarbonyl)amino]methyl}phenoxy]propionic acid ethyl ester;

2-methyl-2-[2-methoxy-4-{[(4-methyl-2-[4-trifluromethylphenyl]-thiazol-5-ylcarbonyl)amino]methyl}phenoxy]propionic acid ethyl ester;

2-methyl-2-[2-methyl-4-{[(4-methyl-2-[4-trifluromethylphenyl]-thiazol-5-ylcarbonyl)amino]methyl}phenoxy]propionic acid ethyl ester;

2-methyl-2-[2-methyl-4-{[(4-methyl-2-[4-trifluromethylphenyl]-thiazol-5-ylcarbonyl)amino]methyl}phenoxy]propionic acid;

2-methyl-2-[2-methyl-4-{[(4-methyl-2-[4-isopropylphenyl]-thiazol-5-ylcarbonyl)amino]methyl}phenoxy]propionic acid ethyl ester;

2-methyl-2-[2-methyl-4-{[(4-methyl-2-[4-isopropylphenyl]-thiazol-5-ylcarbonyl)amino]methyl}phenoxy]propionic acid;

2-methyl-2-[4-{[(5-methyl-2-[4-trifluoromethylphenyl]-thiazol-4-ylcarbonyl)amino]methyl}phenoxy]propionic acid ethyl ester;

2-methyl-2-[4-{[(5-methyl-2-[4-trifluoromethylphenyl]-thiazol-4-ylcarbonyl)amino]methyl}phenoxy]propionic acid;

2-methyl-2-[4-{[(5-methyl-2-[3-trifluoromethylphenyl]-thiazol-4-ylcarbonyl)amino]methyl}phenoxy]propionic acid ethyl ester; and 2-methyl-2-[4-{[(5-methyl-2-[3-trifluoromethylphenyl]-thiazol-4-ylcarbonyl)amino]methyl}phenoxy]propionic acid.

17. A compound selected from:

2-methyl-2-[4-{[(4-methyl-2-[4-trifluoromethylphenyl]-thiazol-5-ylcarbonyl)amino]ethyl}phenoxy]propionic acid ethyl ester;

2-methyl-2-[4-{[(4-methyl-2-[4-trifluoromethylphenyl]-thiazol-5-ylcarbonyl)amino]ethyl}phenoxy]propionic acid;

N-methyl-2-methyl-2-[4-{[(4-methyl-2-[4-trifluoromethylphenyl]-thiazol-5-ylcarbonyl)amino]ethyl}phenoxy]propionic acid;

2-methyl-2-[4-{[(4-methyl-2-[4-tertbutylphenyl]-thiazol-5-ylcarbonyl)amino]methyl}phenoxy]propionic acid;

2-methyl-2-[4-{[(4-methyl-2-[4-isopropylphenyl]-thiazol-5-ylcarbonyl)amino]methyl}phenoxy]propionic acid;

2-methyl-2-[4-{[(4-methyl-2-[4-nitrophenyl]-thiazol-5-ylcarbonyl)amino]methyl}phenoxy]propionic acid;

2-methyl-2-[4-{[(4-methyl-2-[3,4-dichlorophenyl]-thiazol-5-ylcarbonyl)amino]methyl}phenoxy]propionic acid;

2-methyl-2-[4-{[(4-methyl-2-[3-fluoro-4-trifluoromethylphenyl]-thiazol-5-ylcarbonyl)amino]methyl}phenoxy]propionic acid;

2-methyl-2-[4-{[(4-methyl-2-[4-bromophenyl]-thiazol-5-ylcarbonyl)amino]methyl}phenoxy]propionic acid;

2-methyl-2-[4-{[(4-methyl-2-[4-ethylphenyl]-thiazol-5-ylcarbonyl)amino]methyl}phenoxy]propionic acid;

2-methyl-2-[4-{[(4-methyl-2-phenylthiazol-5-ylcarbonyl)amino]methyl}phenoxy]propionic acid;

2-methyl-2-[4-{[(4-methyl-2-[4-fluorophenyl]-thiazol-5-ylcarbonyl)amino]methyl}phenoxy]propionic acid;

2-methyl-2-[4-{[(4-methyl-2-[4-chlorophenyl]-thiazol-5-ylcarbonyl)amino]methyl}phenoxy]propionic acid;

2-methyl-2-[4-{[(4-methyl-2-[4-trifluoromethoxyphenyl]-thiazol-5-ylcarbonyl)amino]methyl}phenoxy]propionic acid;

2-methyl-2-[4-{[(4-methyl-2-[4-methoxyphenyl]-thiazol-5-ylcarbonyl)amino]methyl}phenoxy]propionic acid;

2-methyl-2-[4-{[(4-methyl-2-[4-acetylenylphenyl]-thiazol-5-ylcarbonyl)amino]methyl}phenoxy]propionic acid;

2-methyl-2-[4-{[(4-trifluoromethyl-2-[4-trifluoromethylphenyl]-thiazol-5-ylcarbonyl)amino]methyl}phenoxy]propionic acid;

2-methyl-2-[4-{[(4-methyl-2-[4-trifluromethylphenyl]-oxazol-5-ylcarbonyl)amino]methyl}phenoxy]propionic acid;

2-methyl-2-[4-{[(4-methyl-2-[4-trifluromethyl-2-pyridyl]-thiazol-5-ylcarbonyl)amino]methyl}phenoxy]propionic acid; and 2-methyl-2-[2-methoxy-4-{[(4-methyl-2-[4-trifluromethylphenyl]-thiazol-5-ylcarbonyl)amino]methyl}phenoxy]propionic acid.

18. 2-methyl-2-[4-{[(4-methyl-2-[4-trifluoromethylphenyl]thiazol-5-ylcarbonyl)-amino]methyl}phenoxy]propionic acid.

19. A pharmaceutical composition comprising a compound according to claim 1.

20. A pharmaceutical composition according to claim 19 further comprising a pharmaceutically acceptable diluent or carrier.

21. A method of treating a hPPAR alpha mediated disease or condition in a patient comprising the administration of a therapeutically effective amount of a compound according to claim 1.

22. A method according to claim 21 wherein the hPPAR alpha mediated disease or condition is dyslipidemia, syndrome X, heart failure, hypercholesteremia, cardiovascular disease, type II diabetes mellitus, type I diabetes, insulin resistance, hyperlipidemia, obesity, inflammation, anorexia bulimia, or anorexia nervosa.

* * * * *